US009925081B2

(12) United States Patent
Sedghi

(10) Patent No.: US 9,925,081 B2
(45) Date of Patent: *Mar. 27, 2018

(54) MAGNETIC SATIETY INDUCING SYSTEM

(71) Applicant: Shahriar Sedghi, Macon, GA (US)

(72) Inventor: Shahriar Sedghi, Macon, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,316

(22) Filed: May 4, 2017

(65) Prior Publication Data
US 2017/0231791 A1    Aug. 17, 2017

Related U.S. Application Data

(63) Continuation-in-part of application No. 14/660,846, filed on Mar. 17, 2015, now Pat. No. 9,687,375.

(51) Int. Cl.
*A61F 5/00*        (2006.01)
*A61M 29/02*    (2006.01)

(52) U.S. Cl.
CPC ............ *A61F 5/0089* (2013.01); *A61F 5/003* (2013.01); *A61F 5/004* (2013.01); *A61F 5/0069* (2013.01); *A61M 29/02* (2013.01)

(58) Field of Classification Search
CPC ...... A61F 5/004; A61F 5/0026; A61F 5/0046; A61F 5/0036; A61F 5/003; A61F 5/0069; A61F 5/0089; A61F 5/0003; A61F 5/0006; A61F 5/0073; A61F 5/0013; A61F 2210/009; A61B 2034/302; A61B 2017/00876; A61B 2017/00283; A61M 29/02

See application file for complete search history.

(56) References Cited

U.S. PATENT DOCUMENTS

| | | | | |
|---|---|---|---|---|
| 4,416,272 A * | 11/1983 | Nelkin | ..................... | A41B 9/02 128/95.1 |
| 6,182,288 B1 * | 2/2001 | Kibbee | ..................... | F41H 1/02 2/2.5 |
| 6,406,418 B1 * | 6/2002 | Getek | ..................... | A61N 2/06 600/15 |
| 6,656,194 B1 * | 12/2003 | Gannoe | ................. | A61F 5/0003 604/96.01 |
| 9,687,375 B2 * | 6/2017 | Sedghi | ..................... | A61F 5/004 |
| 2004/0044357 A1 * | 3/2004 | Gannoe | ..................... | A61F 2/04 606/194 |
| 2005/0060789 A1 * | 3/2005 | Waldman | ............... | A41D 27/18 2/205 |
| 2005/0267595 A1 * | 12/2005 | Chen | ..................... | A61F 5/003 623/23.65 |
| 2006/0164280 A1 * | 7/2006 | Nehls | ..................... | G08C 17/02 341/176 |
| 2006/0231110 A1 * | 10/2006 | Mintchev | ............... | A61B 5/053 128/899 |
| 2006/0264982 A1 * | 11/2006 | Viola | ..................... | A61F 5/0036 606/153 |

(Continued)

*Primary Examiner* — Jocelin Tanner
(74) *Attorney, Agent, or Firm* — Select Patents; Ashkon Cyrus

(57) ABSTRACT

A minimally invasive system and method for providing weight loss by inducing the feeling of satiety whereby an intragastric device is inserted into the gastric lumen via the esophagus and an external magnetic device is used as needed to magnetically attract the intragastric device towards the inner wall of the stomach and impart tactile stimulation sufficient to induce the feeling of satiety.

20 Claims, 20 Drawing Sheets

(56) References Cited

U.S. PATENT DOCUMENTS

| | | | |
|---|---|---|---|
| 2008/0172079 A1* | 7/2008 | Birk | A61F 5/0036 |
| | | | 606/192 |
| 2010/0168782 A1* | 7/2010 | Hancock | A61F 5/003 |
| | | | 606/192 |
| 2012/0095499 A1* | 4/2012 | Babkes | A61F 5/0033 |
| | | | 606/198 |
| 2013/0018215 A1* | 1/2013 | Snider | A61F 2/915 |
| | | | 600/1 |
| 2014/0276307 A1* | 9/2014 | Landtbom | A61F 5/028 |
| | | | 602/19 |
| 2014/0276941 A1* | 9/2014 | Rodriguez-Navarro | A61B 19/22 |
| | | | 606/130 |

* cited by examiner

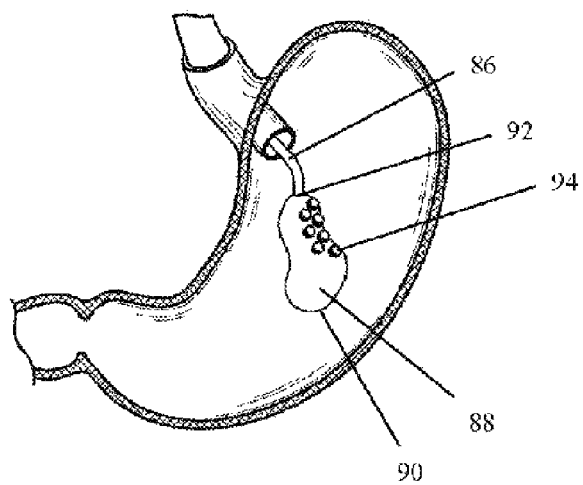
FIG. 6A
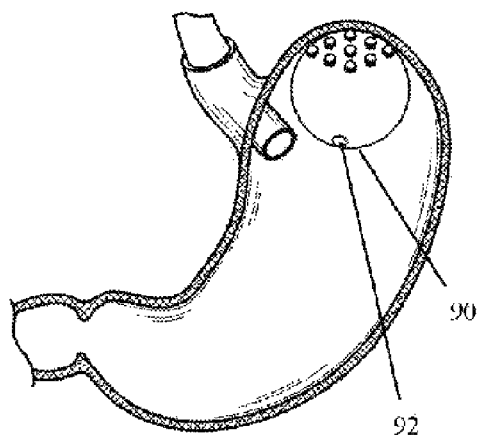
FIG. 6B
FIG. 6C
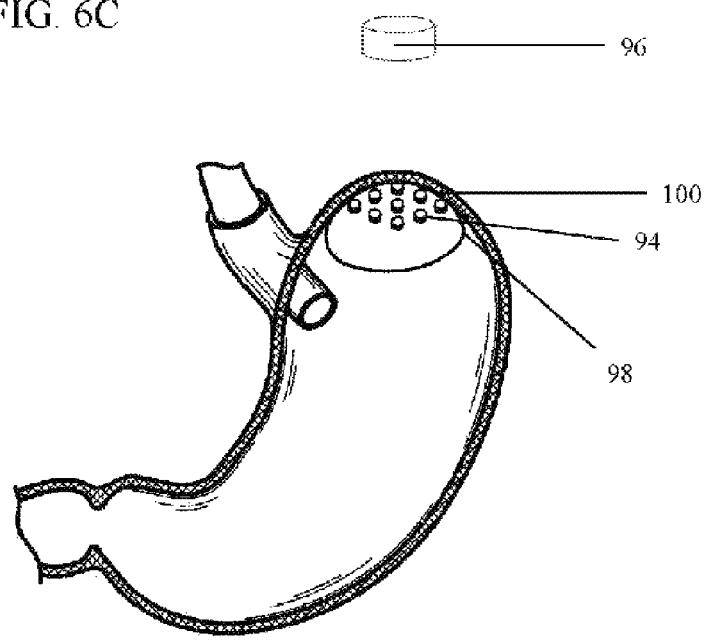

400
403
402
404

404
403

MAGNETIC SATIETY INDUCING SYSTEM

RELATED APPLICATIONS

This patent application is a continuation-in-part of U.S. patent application Ser. No. 14/660,846, which was filed on Mar. 17, 2015, entitled "MAGNETIC SATIETY INDUCING SYSTEM"

FIELD OF THE INVENTION

The present invention relates to obesity treatment generally and, more particularly, to a method of magnetically positioning a deployable device in the gastric lumen to induce the feeling of satiety.

DESCRIPTION OF RELATED ART

Morbid obesity is a major medical problem affecting millions of people. Obese patients currently undergo several types of surgery to either staple or tie off portions of the stomach, small intestine, and/or bypass portions of the same to reduce both the amount of food desired by the patient and absorbed by their intestinal tract. Current methods for achieving these results include laparoscopic banding, surgical bypass, and gastric stapling. These methods often necessitate incisions and general anesthesia, and may cause long- or short-term complications.

Less invasive endoscopic procedures are also used to assist weight loss, and have primarily focused on placement of a balloon or other space-occupying device in the patient's stomach to provide a continual feeling of fullness and consequential reduction in food intake, often in conjunction with behavioral modification programs. To accomplish these procedures, an endoscope is generally utilized to guide the space-occupying device through the patient's mouth, down the esophagus, and into the stomach before relinquishing control of the device for some 4-12 months, and endoscopically retrieving it thereafter.

While these methods are clinically efficacious in many cases, neither of them facilitate non-invasive post-operation adjustments and both suffer from unsustained weight loss due to the body's natural adaptation to the changes made along with complications including improper positioning of devices, stretching of the intestinal tract, bowel obstruction, and stomach erosion requiring invasive intervention. Inasmuch as these intragastric devices remain uncontrolled, unattached, and free-floating within the stomach, undesired migration and bowel obstruction are likely to continue causing technical difficulties for patients and clinicians, impeding removal efforts, and necessitating additional invasive procedures.

While the present invention discloses improvements over the prior art including the use of magnetism to retain control of intragastric devices after implantation, and using that control to induce the feeling of satiety in patients, the well-known prior art principles of magnetism, electromagnetism, and techniques for minimally invasive transesophageal insertion and removal of intragastric devices will not be discussed in greater detail than necessary to enable persons of ordinary skill in the art to make and use the subject matter of the invention.

SUMMARY OF THE INVENTION

The present invention provides several novel magnetic devices capable of inducing the feeling of satiety from inside the stomach, as well as external magnetic devices capable of intermittently adjusting, positioning, and attracting their intragastric counterparts from outside the body. This retention of non-invasive control over an intragastric device after insertion enables medical practitioners, patients, and automated medical devices to magnetically stimulate and even stretch a specific portion of the stomach, such as the fundus, where satiety nerves are maximal. In addition to patients who may otherwise be treated surgically as morbidly obese, the invention provides greater access to minimally invasive weight loss procedures for patients who are only moderately overweight or obese, reducing the risks associated with more invasive procedures.

BRIEF DESCRIPTION OF THE DRAWINGS

FIG. 6A is a perspective view of an inflatable intragastric device in the deflated state during transesophageal insertion.

FIG. 6B is a perspective view of an inflatable intragastric device in the inflated state.

FIG. 6C is a perspective view of an inflated intragastric device being attracted to an external magnetic device.

DETAILED DESCRIPTION

The present invention discloses intragastric medical devices which may be implanted within a patient's body without surgery, and controlled remotely with external devices using the forces of magnetic attraction and repulsion. Deployable devices that may be inserted into the stomach of a patient include devices containing flexible or rigid magnetic materials in a variety of shapes, sizes, and orientations. Devices whose structure is formed from a flexible and resilient material deploy immediately when they are no longer restrained. Although deployable devices can be restrained in many ways, this is often effectuated by the patient's esophagus, an overtube, or sutures binding the device in the collapsed position during transesophageal insertion or removal, which are endoscopically removed from the device inside the stomach. Fluid-filled devices are deployed by filling their bladders with fluid.

The orientation and position of such devices, e.g., a collapsible frustacone-shaped device, may be adjusted remotely with an external device containing magnetic material. The magnetic materials of the internal and external devices may include any magnets, magnetizable materials, and ferrous metals apparent to persons of ordinary skill in the art such as iron, nickel-iron, silicon-iron, cobalt-iron, neodymium, magnetic powder, amorphous and nanocrystalline alloys, ferrite powder, rubber polymer resins, mixtures and alloys of the foregoing, and for external devices, electromagnets. Such magnetic materials may be positioned on the interior or exterior surface of a device, or may be integral thereto.

The disclosed systems, combinations of magnetic materials capable of attracting one another, devices, and methods are susceptible to implementation in various embodiments and the disclosure of specific embodiments is not intended to limit the scope of the invention as claimed unless expressly specified. The invention will now be described in connection with certain embodiments and drawings so that it may be more fully understood. With specific reference to the embodiments and figures in detail, it is stressed that the particulars presented are by way of example for purposes of illustrative discussion of embodiments of the present invention only and are presented to provide what is believed to be the most readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1A:
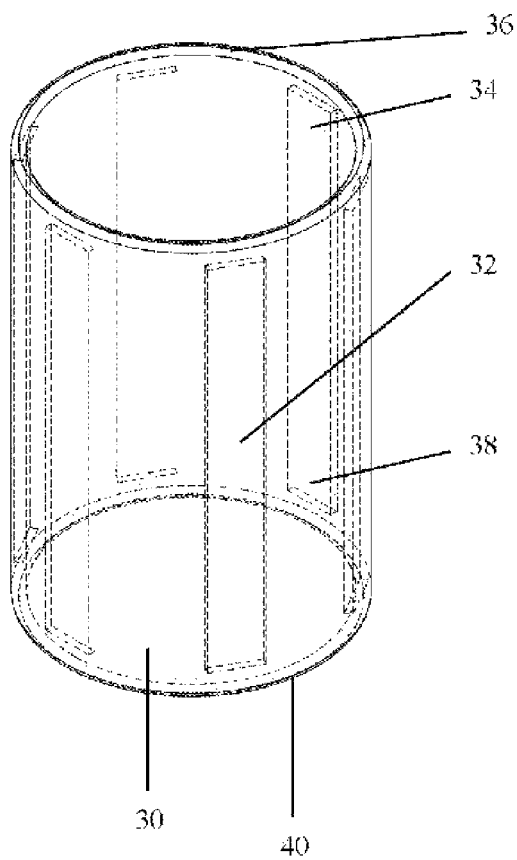
FIG. 1A is a perspective view of a collapsible tubular intragastric device.
Figure 1B:
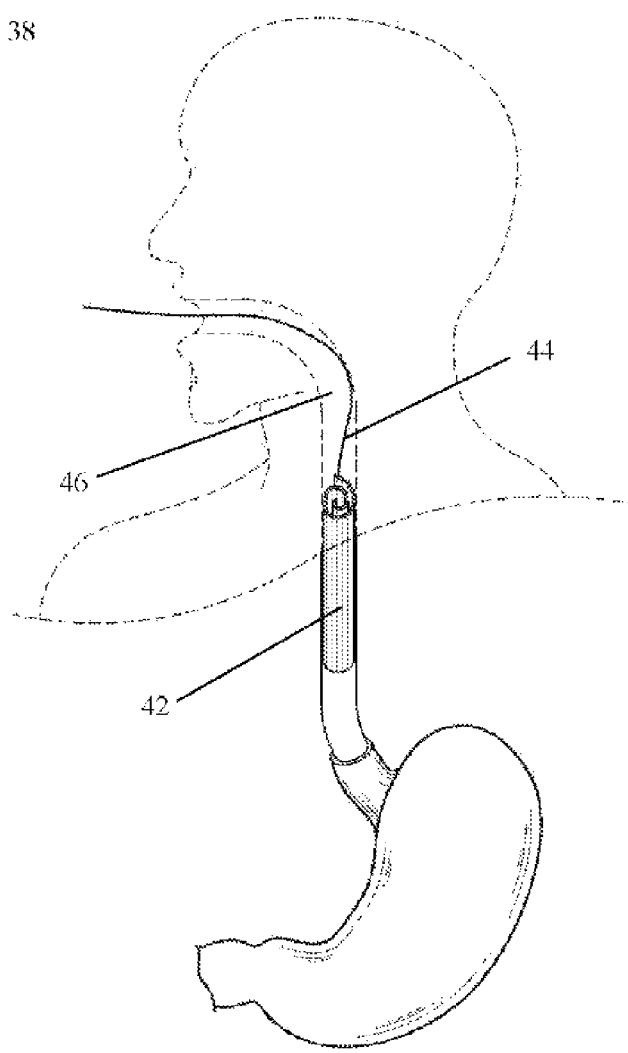
FIG. 1B is a perspective view of the esophageal insertion of a collapsed intragastric device.

A first embodiment of an intragastric device is presented in FIG. 1A, which shows a perspective view of a tubular intragastric device in its default deployed state, during which its flexible and resilient tubular structure (30) forms a hollow cylindrical passage, around which 6 sealed compartments capable of containing magnetic materials are circumferentially distributed within the tubular structure's flexible and resilient material, containing 6 bar magnets (32) with their north poles (34) facing the top of the device (36) and south poles (38) facing the bottom of the device (40). FIG. 1B shows the device of FIG. 1A in the collapsed state (42) reversibly attached to an endoscope (44) that is pushing the device through the patient's esophagus (46). Once such a resilient collapsible device exits the esophagus, the device's resilient and flexible structure reverts to its natural deployed state, as shown in FIG. 1A. While endoscopic insertion is disclosed in FIG. 1A, several other methods of insertion will be apparent to the persons of ordinary skill in the art, as will the use of fluoroscopic guidance when advantageous. Without limitation, alternative insertion methods may include the placement of an endoscope in the stomach, passing a guidewire into the stomach through the endoscope's working channel, redrawing the endoscope, and passing an intragastric device over the guidewire with a delivery caster. Similarly, practitioners may load an overtube onto an endoscope used to place the overtube from the mouth to the distal esophagus or stomach before redrawing the endoscope and passing the intragastric device through the overtube's lumen, which may also accommodate any other instruments used to support the intragastric device.

Figure 2A:
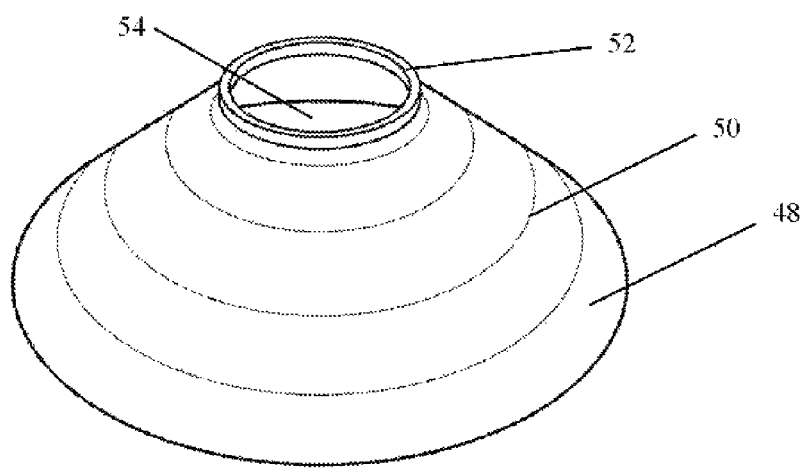
FIG. 2A is a perspective view of a ring magnet embodiment of the collapsible intragastric device.
Figure 2B:
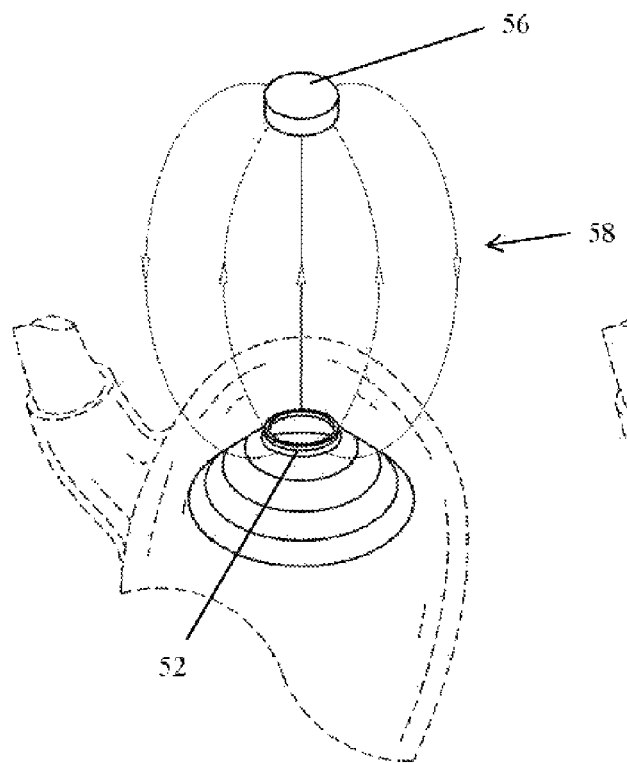
FIG. 2B is a perspective view of a ring magnet embodiment of the collapsible intragastric device being subjected to slight magnetic force with an external magnet.

Referring now to FIG. 2A, the collapsible intragastric device comprises a frustacone-shaped structure (48) which is primarily constructed from a resilient and flexible material with textured ridges (50) encircling a ring magnet (52) small enough in diameter to slide down a patient's esophagus and containing a hollow central passage (54). FIG. 2B shows the collapsible intragastric device in a patient's stomach with an external magnet (56) positioned outside the patient's body just close enough to the intragastric device to create a slight attractive force between the intragastric device's ring magnet (52) and external magnet (56), as represented by the magnetic field lines (58) running from the external magnet's north pole to the ring magnet's south pole and from the ring magnet's north pole to the external magnet's south pole.

Figure 2C:
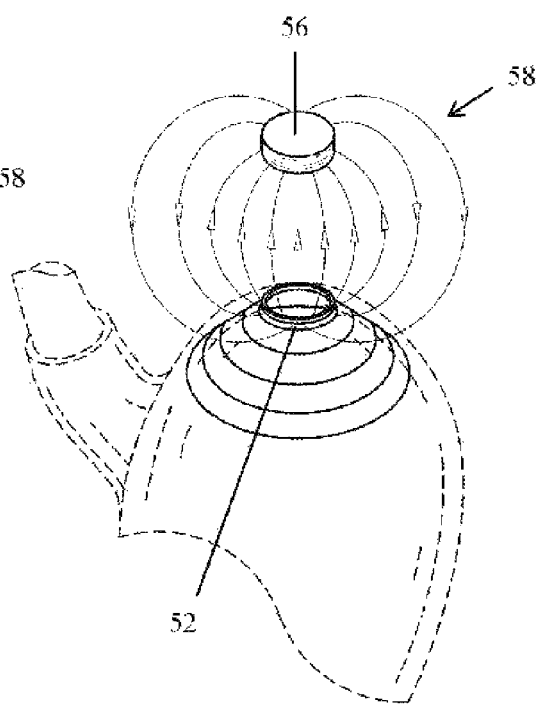
FIG. 2C is a perspective view of the intragastric device in a patient's stomach being subjected to moderate magnetic force with an external magnet.

FIG. 2C shows the external magnet (56) positioned outside the patient's body and close enough to the intragastric device to create a strong attractive force between the ring magnet (52) and the external magnet (56) represented by a larger number of magnetic field lines (58) between the devices.

Figure 3A:
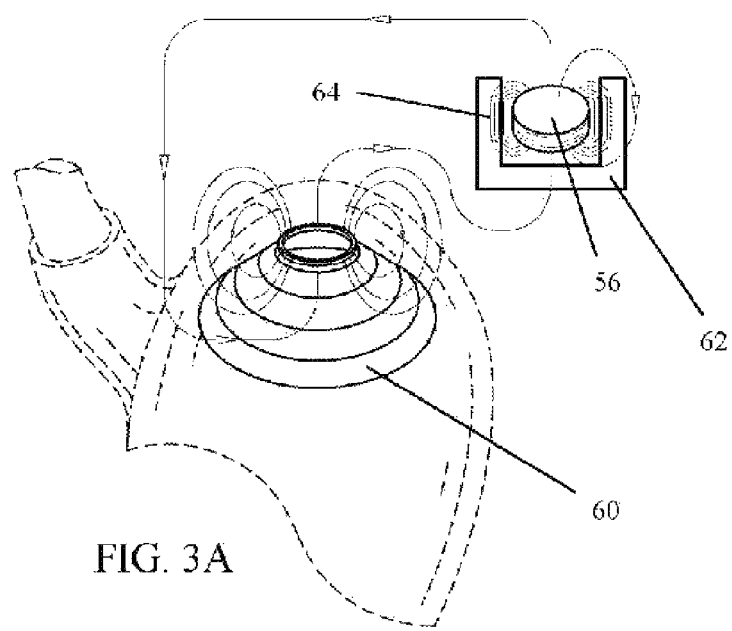
FIG. 3A is a perspective view of an external shell of high magnetic permeability diverting most of an external magnet's field lines away from an intragastric device.
Figure 3B:
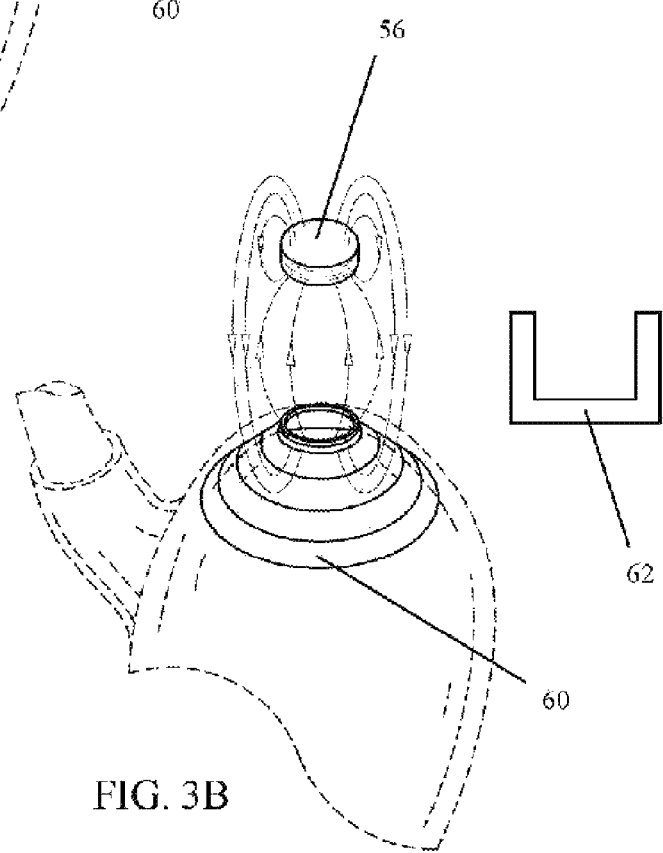
FIG. 3B is a perspective view of an external magnet attracting an intragastric device after removal from a shell of high magnetic permeability.

Another embodiment of the satiety-inducing system's external components seeks to address the need for safety and convenience of adjustability. For example, the more than 50-fold increase in magnetic field strength that can occur as the separation distance between magnets is reduced from 13 inches to 2 inches comes with acknowledged risks of discomfort, injury, and attractive forces great enough to impair patients' ability to move external magnets away from their torso. In addition to maintaining a safe distance between magnetic materials, magnetic field lines can be diverted away from the stomach with a moveable shell, case, or sleeve of high magnetic permeability that can be slid into place to reduce attractive force. FIG. 3A shows a an external magnet (56) close enough to an intragastric device (60) to create a strong attractive force, which is nonetheless producing only a nominal pulling force due to the positioning of the external magnet within a shell of high magnetic permeability (62), which has diverted the majority of the external magnet's field lines (64) away from the intragastric device (60). FIG. 3B shows a strong attractive force occurring between the intragastric device (60) and external magnet (56) of FIG. 3A, as applied to the stomach wall by the intragastric device, due to the removal of the external magnet (56) from the shell of high magnetic permeability (62) despite maintaining a distance between the intragastric and external devices similar to that in FIG. 3A. Finally, when a permanent reduction in the strength of the magnetic field emanating from the external device in a particular direction is desired, such as to prevent interference with other electronic devices, a shell, case, sleeve, or coating of high magnetic permeability may be affixed to a smaller portion of the external device to provide these benefits without necessitating the removal depicted by FIGS. 3A-B in order to attract an intragastric device.

Figure 4A:
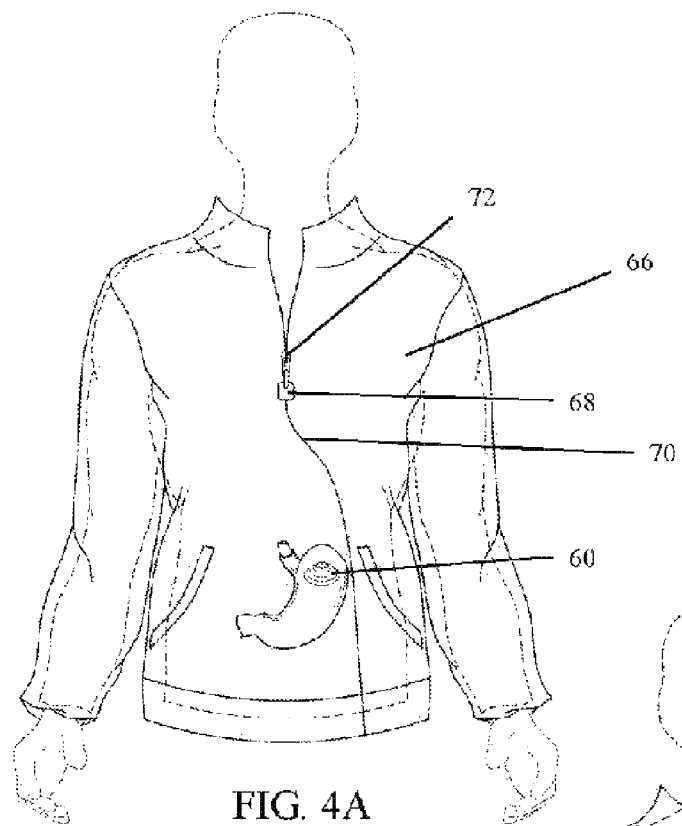
FIG. 4A is a perspective view of a piece of magnetic apparel in the unactivated position.
Figure 4B:
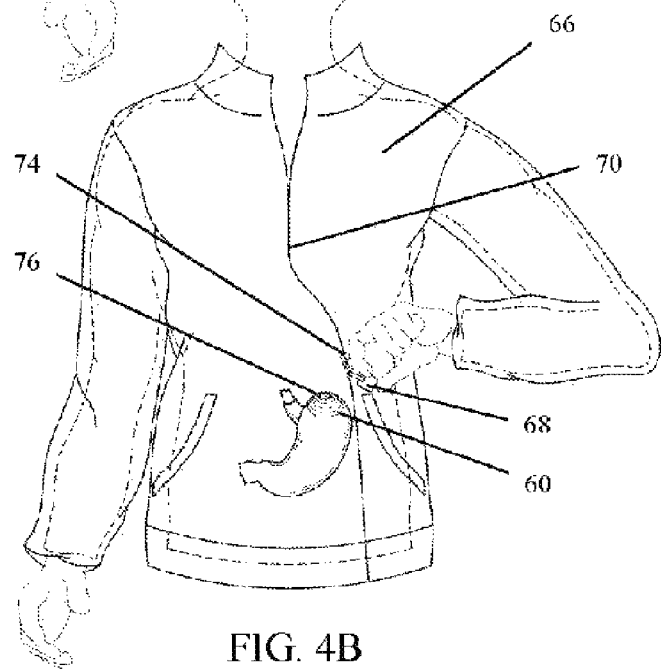
FIG. 4B is a perspective view of a piece of magnetic apparel in the activated position.

Yet another embodiment of the satiety-inducing system addresses the need for predictable positioning of the external magnet, as well as practical means for carrying it around throughout the day. FIG. 4A shows a piece of apparel (66) with an external magnet (68) attached to a zipper (70) in the upper position (72), which is a large enough distance from the intragastric device (60) to create only a nominal pulling force. FIG. 4B shows a piece of apparel (66) with an external magnet (68) attached to a zipper in the lower position (74), which is close enough to the intragastric device (60) to create a strong pulling force between the external magnet and intragastric device, which is applied in the form of tactile stimulation to the inner stomach wall (76) to induce the feeling of satiety. Finally, components of high magnetic permeability such as those depicted in FIGS. 3A-B and methods of preventing undesired magnet and zipper travel apparent to persons of ordinary skill in the art such as pockets, buttons, and hook-and-loop fasteners may be integrated into the apparel. While compounds of high magnetic permeability may be integrated into any part of the apparel, an exemplary application can occur at the upper position (72) for a number of reasons, including diversion of magnetic field lines away from the intragastric device to further reduce the pulling force, reduction of the travel distance between the upper and lower positions, and prevention of magnetic interference with, or attraction to, other magnetically sensitive objects.

Figure 5A:
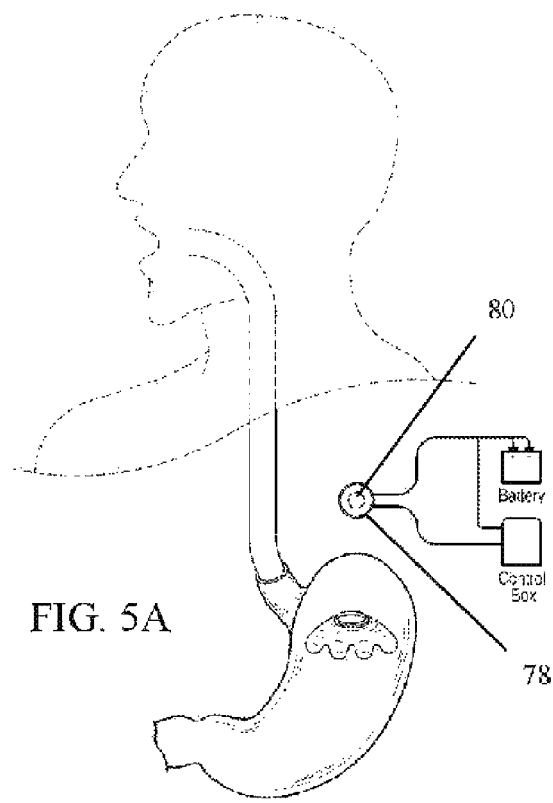
FIGS. 5A-B are perspective views of an external electromagnet system.
Figure 5B:
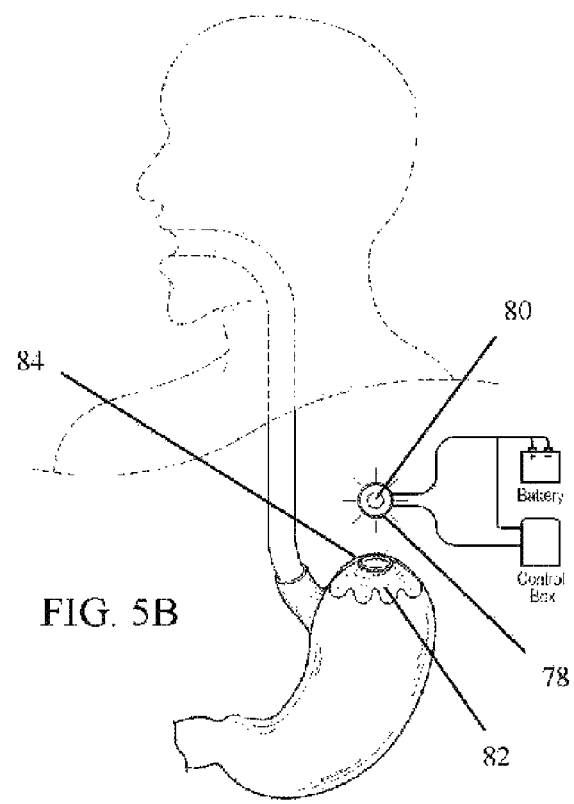

When an alternative to conventional magnetic material in the external portion of the satiety-inducing system is desired, electromagnets may also be used. FIG. 5A shows an external electromagnet system which comprises an electromagnet (78) with ferromagnetic core (80) and a control box containing an electron throttle that is completely barring the flow of electrons from the battery into the electromagnet. FIG. 5B shows the external electromagnet of FIG. 5A with an electric current flowing from the battery into the electromagnet to create a strong enough magnetic field to attract the collapsible frustacone-shaped intragastric device (82) towards, and impart stimulating force upon, the inner stomach wall (84), to induce the feeling of satiety.

For applications where buoyancy, volumetric distention, or other attributes of inflatable devices are deemed advantageous, inflatable bladders may be used. FIG. 6A shows an intragastric device in the deflated state for transesophageal insertion and removal with an endoscope (86) that pumps fluid into or out of the bladder (88) formed by the device's flexible skin (90) through a sealing valve (92) to facilitate intragastric device deployment, and may optionally include a snare loop to streamline transesophageal retrieval. The skin also includes embedded magnets (94) which optionally protrude from the flexible skin to augment the tactile stimulation imparted upon the inner stomach wall by the device. FIG. 6B shows the intragastric device of FIG. 6A in the inflated state. FIG. 6C shows the inflated intragastric device of FIG. 6B in close proximity to an external magnet (96), creating an attractive force between the devices sufficient to cause deflection (98) of the intragastric device's flexible skin as it is pulled towards, and applies stimulating force to, the inner stomach wall (100), to induce the feeling of satiety. Although FIG. 6A depicts an endoscope, it is not intended as the sole method of insertion and removal, and, along with other embodiments of the invention, several methods of intragastric device insertion and removal will be apparent to persons of ordinary skill in the art, and any appropriate methods may be used. For example and without limitation, some of the equipment that may be helpful in transesophageal insertion and removal of intragastric devices may include biopsy forceps, overtubes, guidewires, banding devices, sutures, suction cylinders, endoscopic needles, endoscopic scissors, endoscopic magnets, and endoscopic lumens through which transesophageal fluid transfer may be accomplished.

Figure 7A:
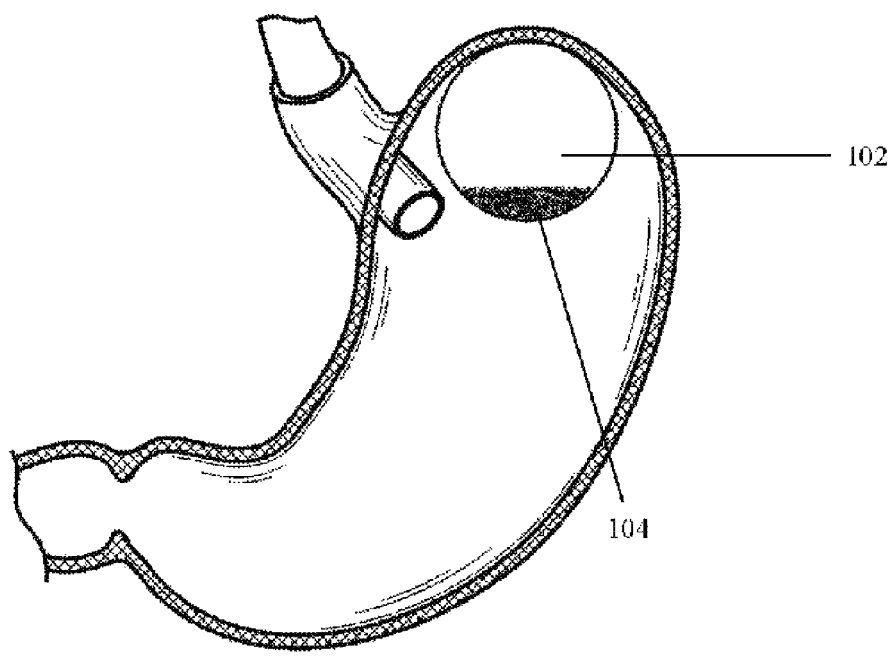
FIG. 7A is a perspective view of an inflatable intragastric device containing magnetic powder.
Figure 7B:
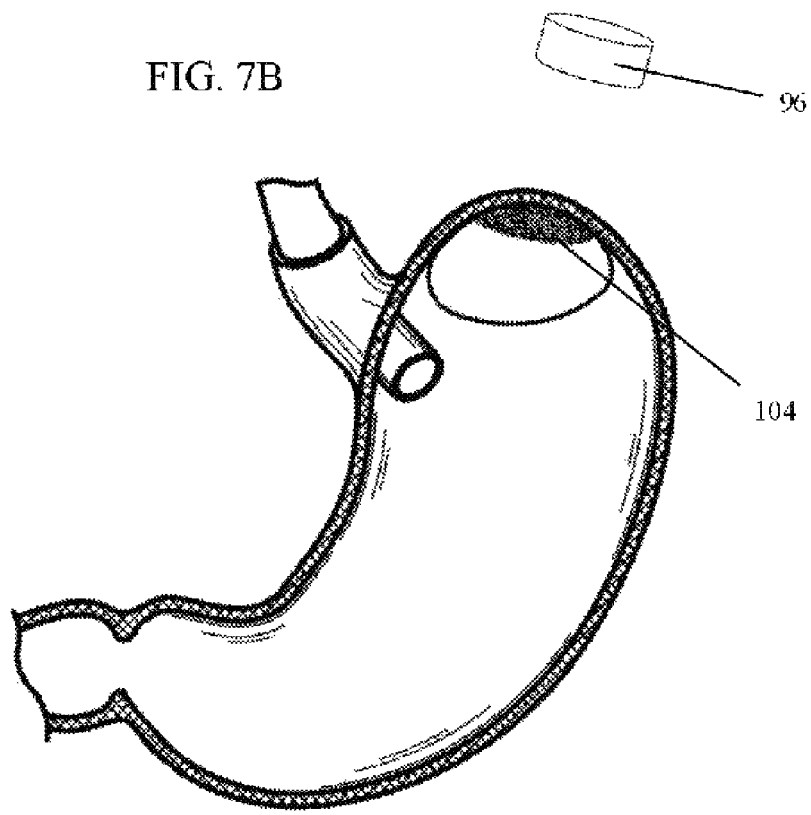
FIG. 7B is a perspective view of an inflated intragastric device being attracted to an external magnetic device.

Biocompatible materials with resilient or flexible properties such as a polymer may be used in any device, such as the flexible skin (90) depicted in FIGS. 6A-C. Suitable polymers include without limitation, hydrogels, silicone, polyethylene, polypropylene, polyurethane, polycaprolactone, polytetrafluoroethylene (PTFE), copolymers, magnetic polymers, combinations of the foregoing optionally including magnetic materials, and the like. Similarly, while biocompatible fluids such as saline solution are desirable for use in intragastric devices, acceptable fluids without limitation include air, liquids, gels, and combinations thereof. FIG. 7A shows an inflated intragastric device (102) that is inserted into the stomach and inflated by the same endoscopic process as shown in FIG. 6A. Unlike the intragastric device shown in FIG. 6A, the magnetic powder (104) contained within this intragastric device is not affixed to the skin of the device and is free to move within the confines of the bladder's inner wall. FIG. 7B shows the inflated intragastric device of FIG. 7A with an external magnet (96) in close proximity to the stomach, creating an attractive force between the magnetic powder (104) and external magnet sufficient to pull the intragastric device towards, and impart stimulating force upon, the inner stomach wall, inducing the feeling of satiety.

For this and all deployable intragastric devices, substances capable of alerting a patient or doctor that a device has failed may be embedded in the device, preferably at the most likely points of failure, such as the bladder of an inflatable device. While all substances and mechanisms of failure notification known to persons of ordinary skill in the art may be used, exemplary substances without limitation may include methylene blue as well as dyes capable of altering a patient's stool or urine in a manner sufficient to provide notice of latent device failure, or providing intragastric coloration that can be observed through an endoscope to aid in the process of ascertaining the location, type, and severity of device abnormalities.

Figure 8:
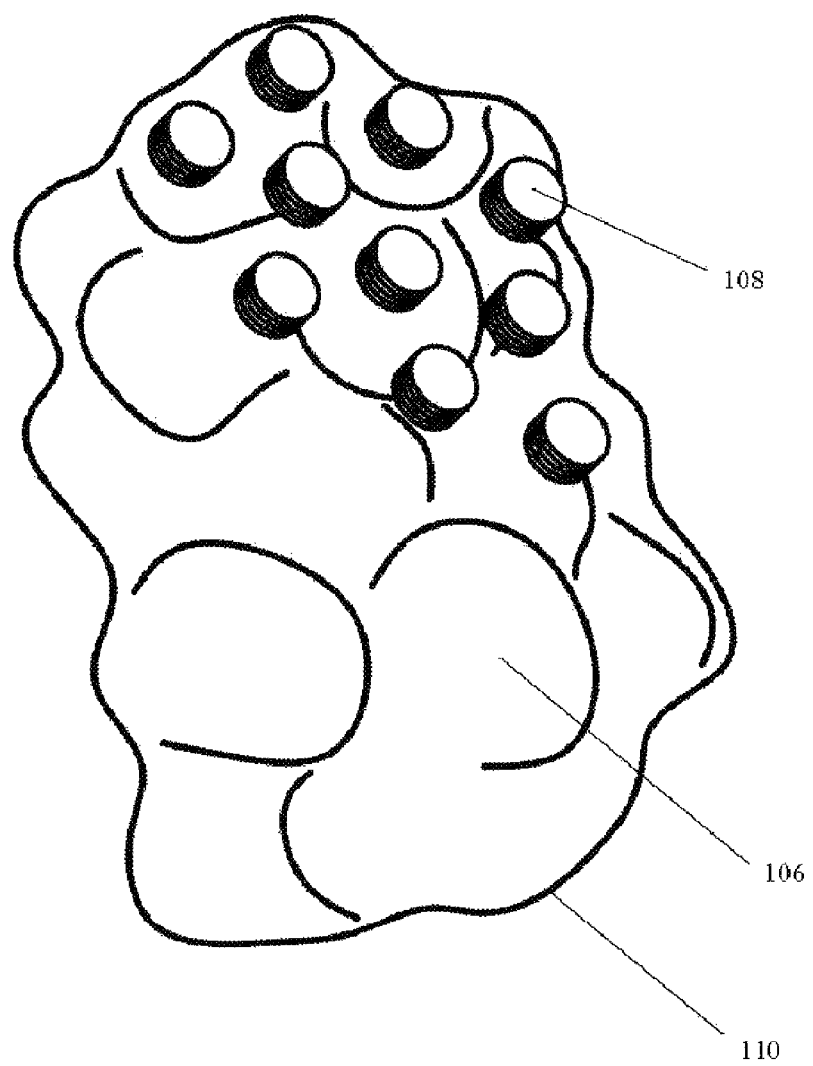
FIG. 8 is a perspective view of an inflated intragastric device with rounded protrusions.

FIG. 8 shows an alternative embodiment of an inflatable intragastric device constructed primarily from a flexible and resilient skin which constitutes a fluid bladder that can either be endoscopically filled and drained within the stomach in the manner shown in FIGS. 6A-C, or manufactured in a size small enough to stretch into a substantially cylindrical shape to slide through the esophagus in the filled state. The device contains variably sized rounded protrusions (106) and hemispherically localized magnets (108) integrated into the device's flexible skin (110), which protrude from the device to impart tactile stimulation upon the stomach wall and induce the feeling of satiety.

Figure 9:
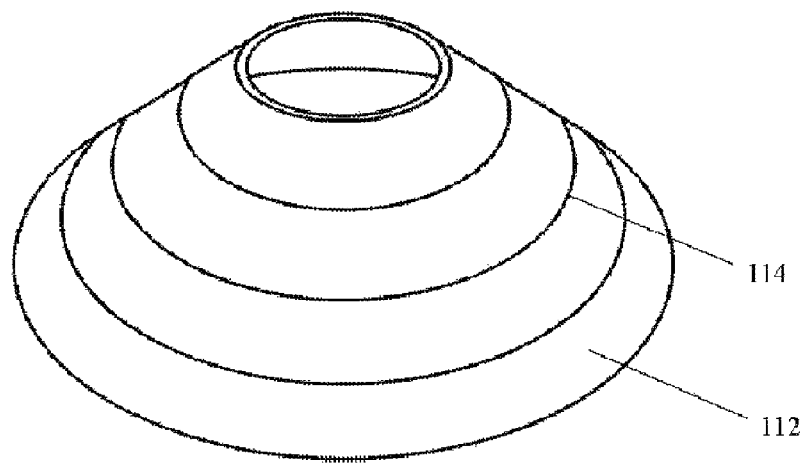
FIG. 9 is a perspective view of a collapsible frustacone-shaped intragastric device.

When a more uniform distribution of magnetic material throughout the device is desired, or simplifies the manufacturing process, fine magnetic materials such as magnetic powder may be integrated in the flexible and resilient material that forms the primary structure of the device. As is the case with all embodiments, in the event that this process forms a material that is not biocompatible, the device may be coated with a biocompatible material. FIG. 9 shows a collapsible frustacone-shaped intragastric device constructed entirely from a flexible and resilient magnetic compound (112) with textured ridges (114) which can be collapsed for transesophageal insertion into, and removal from, the stomach. As is the case with all other devices, magnetic materials may be added to an endoscope to help facilitate the transesophageal insertion and retrieval of intragastric devices.

Figure 10A:
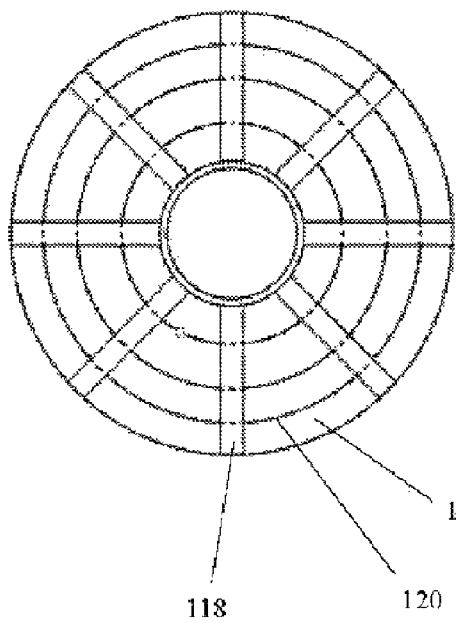
FIG. 10A is a top plan view of a collapsible frustacone-shaped intragastric device with integrated bar magnets.
Figure 10B:
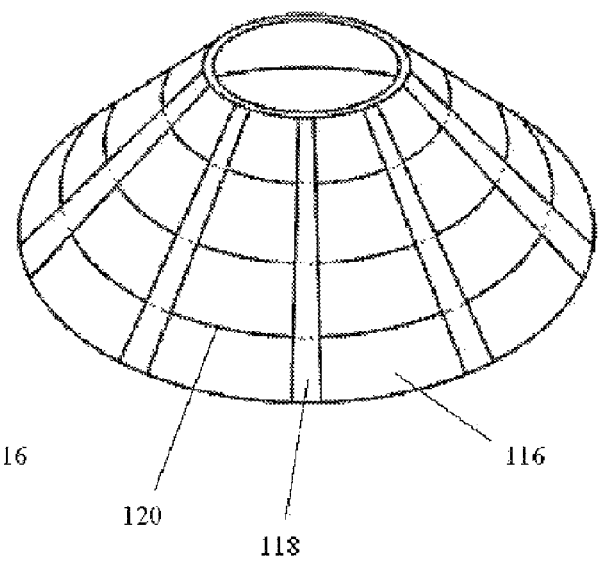
FIG. 10B is a perspective view of a collapsible frustacone-shaped intragastric device with integrated bar magnets.

FIG. 10A shows a collapsible intragastric device which comprises a flexible and resilient frustacone-shaped structure (116) with 8 circumferentially distributed bar magnets (118) embedded in the frustacone-shaped structure with three suture loops (120) traveling through the upper, mid, and lower portion of each bar magnet, securing them both to one another and the frustacone-shaped structure within which they are embedded. FIG. 10B is a top plan view of the intragastric device of FIG. 10A.

Figure 11A:
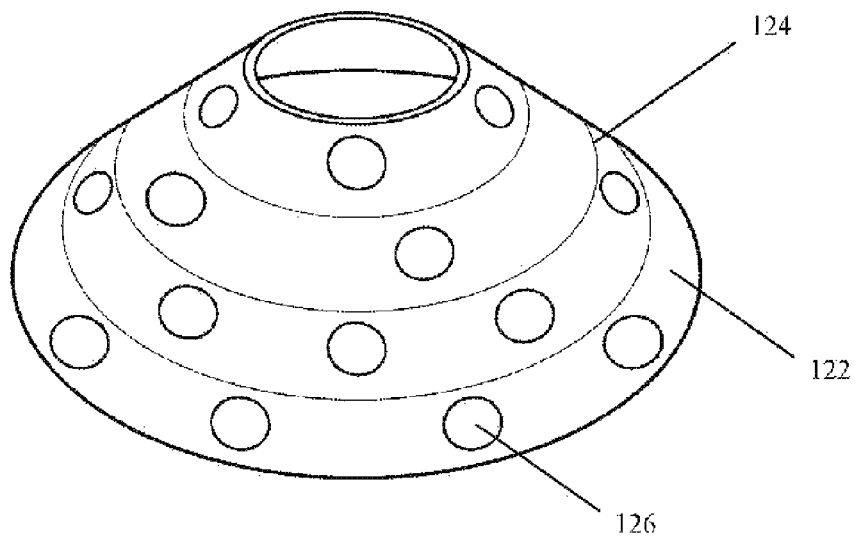
FIG. 11A is a perspective view of a collapsible frustacone-shaped intragastric device with integrated disc magnets.
Figure 11B:
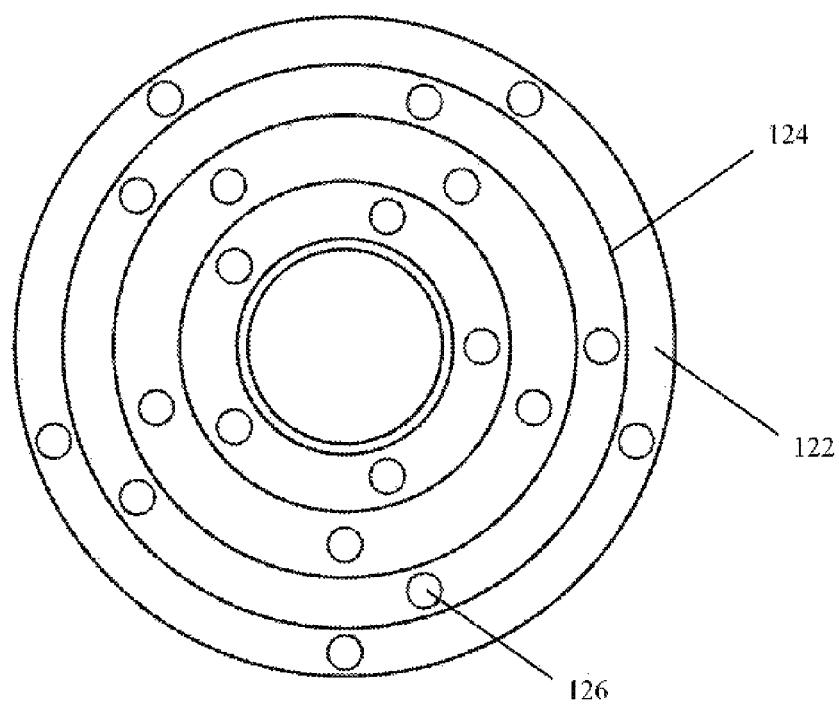
FIG. 11B is a top plan view of a collapsible frustacone-shaped intragastric device with integrated disc magnets.

FIG. 11A shows a collapsible intragastric device which comprises a flexible and resilient frustacone-shaped structure (122) with raised textured ridges (124) and embedded disc magnets (126) circumferentially distributed inside of the biocompatible frustacone-shaped structure. FIG. 11B is a top plan view of the intragastric device of FIG. 11A.

Figure 12:
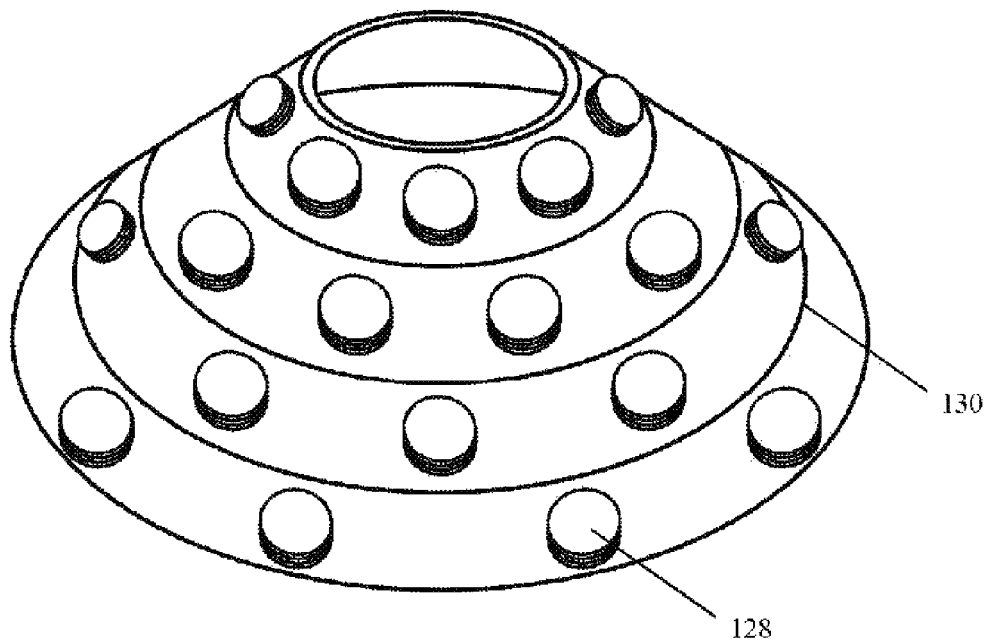
FIG. 12 is a perspective view of a device comprising the flexible and resilient frustacone-shaped structure of FIG. 11A outfitted with protruding cylindrical magnets in lieu of flush embedded disc magnets.

FIG. 12 shows an intragastric device comprising the flexible and resilient frustacone-shaped structure of FIG. 11A, outfitted with protruding cylindrical magnets (128), embedded resilient loops (130), and a biocompatible coating capable of stimulating the inner wall of a patient's stomach to induce the feeling of satiety.

Figure 13:
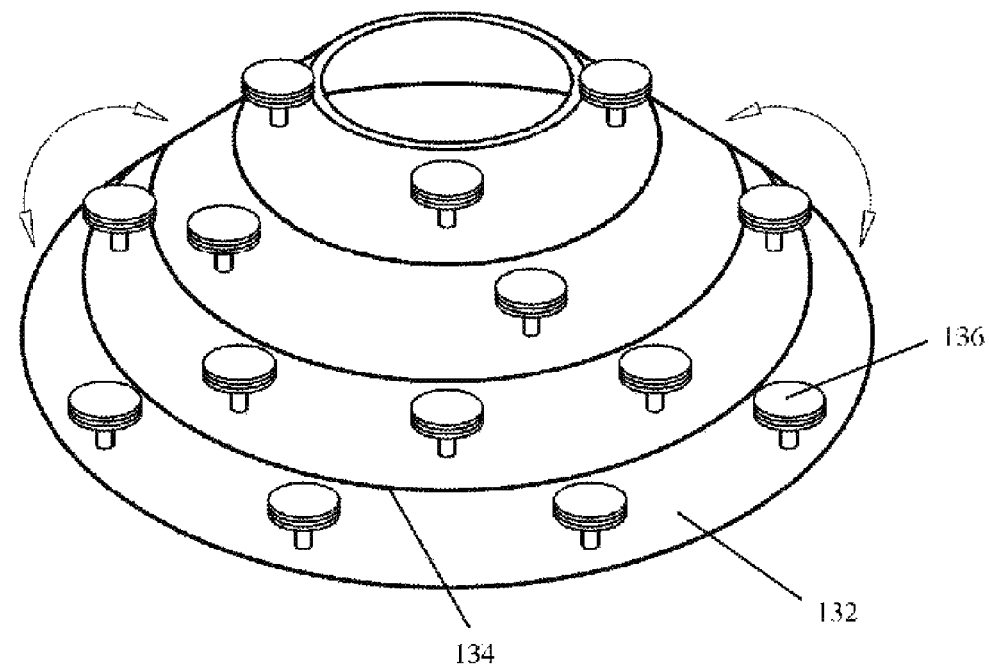
FIG. 13 is a perspective view of a collapsible frustacone-shaped intragastric device with protruding swiveling magnets.

FIG. 13 shows a collapsible intragastric device which comprises a flexible and resilient structure in a frustacone shape (132) with embedded resilient loops (134) and swiveling magnets with a biocompatible coating (136) protruding from the outer surface of the structure to impart tactile stimulation upon the inner wall of a patient's stomach and induce the feeling of satiety.

When an even greater degree of change to magnetic materials' orientation relative to the device within which they are installed is desired, magnetic materials may be confined within a designated section of a device without further restricting their movement. Allowing magnets to shift in this manner can ensure external devices' ability to magnetically attract intragastric devices regardless of their orientation. In other words, this manner of construction allows a magnetic device's polarity to change even when the orientation of the device cannot change.

Figure 14A:
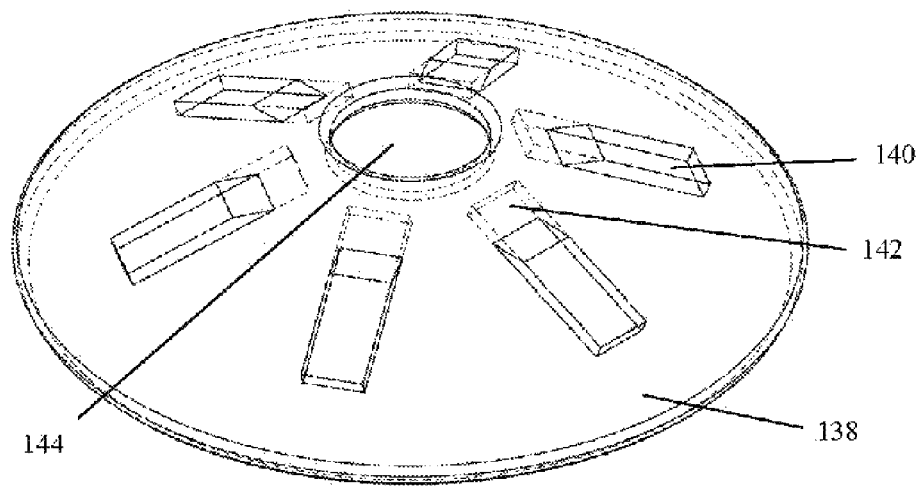
FIGS. 14A-C depict a frustacone-shaped collapsible intragastric device with embedded compartments containing magnetic powder.
Figure 14B:
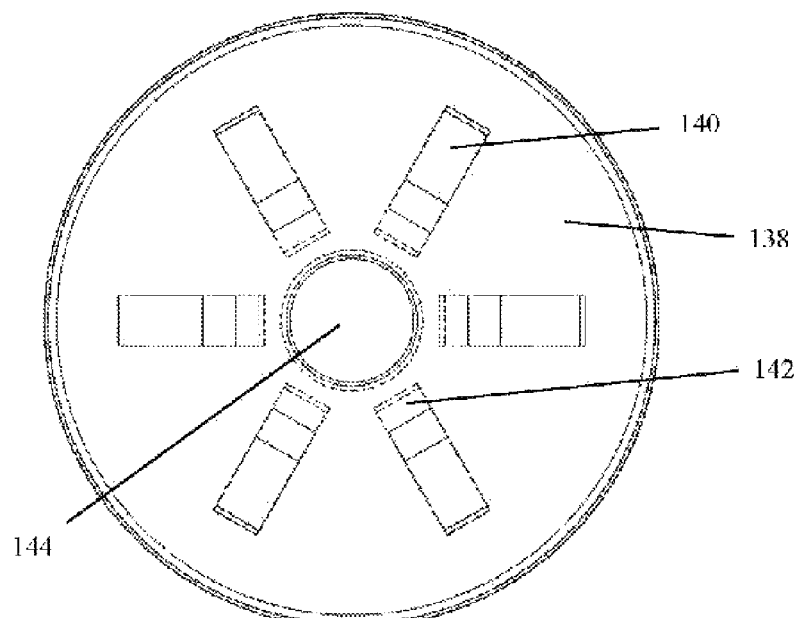
Figure 14C:
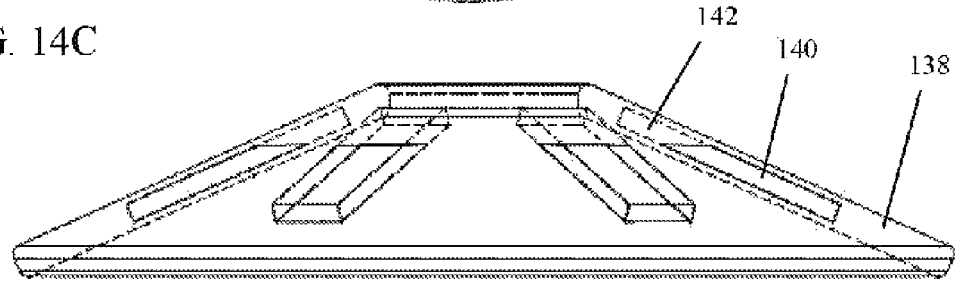

FIG. 14A is a perspective view of a collapsible intragastric device comprising a flexible and resilient frustacone-shaped structure (138) that envelopes 6 sealed compartments (142) capable of securing magnetic materials, which are partially filled with unrestrained magnetic powder (140) which is not being subjected to any external magnetic fields. The intragastric device also contains a hollow central core (144) through which stomach contents may pass and within which an endoscope may be attached for transesophageal insertion and retrieval. FIG. 14B is a bottom plan view of the intragastric device depicted in FIG. 14A. FIG. 14C is a side elevation view of the intragastric device depicted in FIG. 14A. While depicted in an intragastric embodiment, this method of construction is equally applicable to external magnetic devices.

Figure 15A:
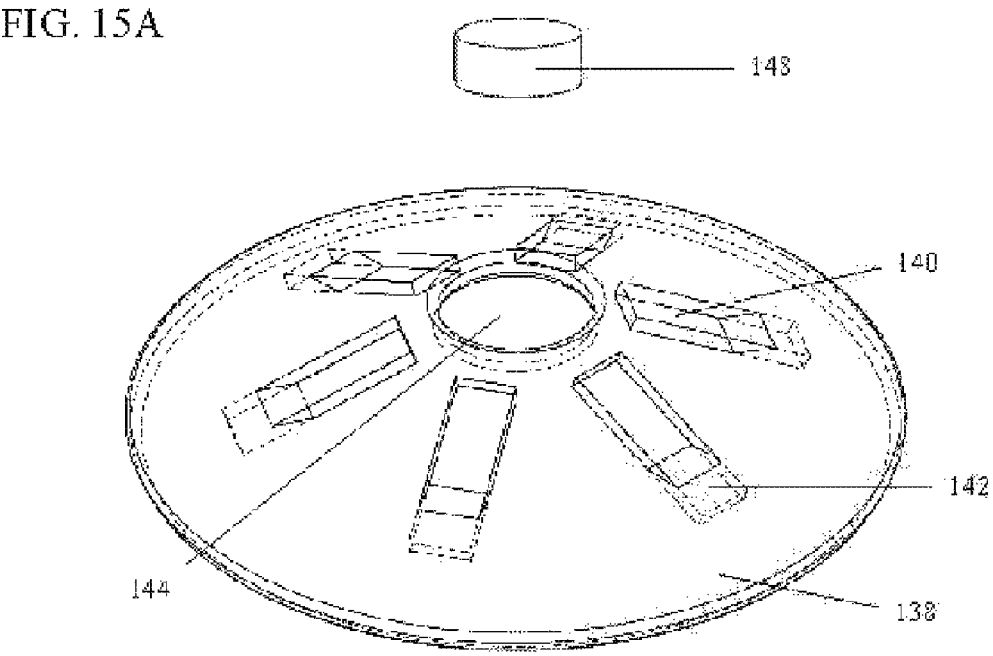
FIGS. 15A-C depict the frustacone-shaped collapsible device of FIGS. 14A-C interacting with an external device's magnetic field.
Figure 15B:
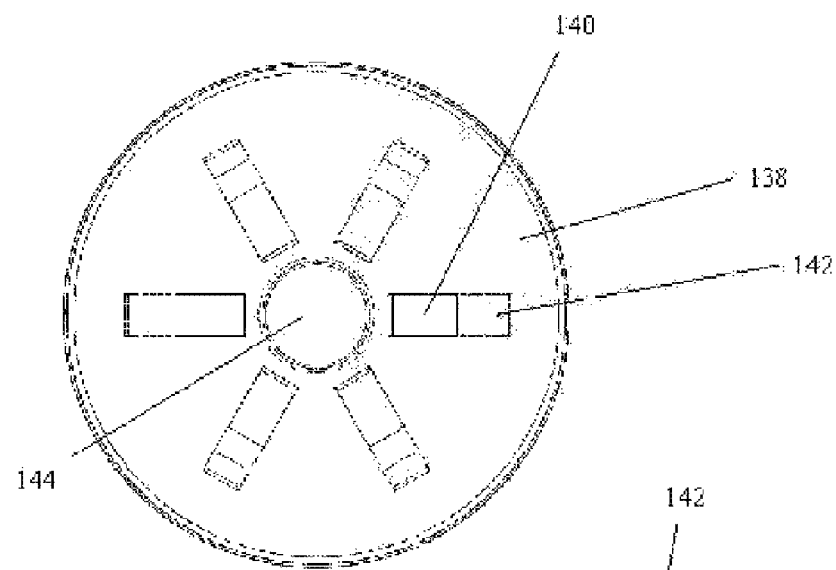
Figure 15C:
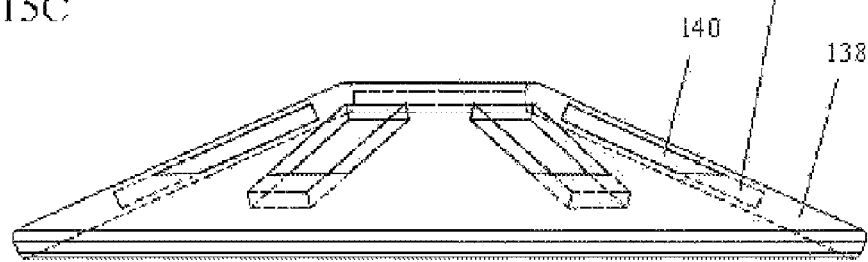
Figure 16A:
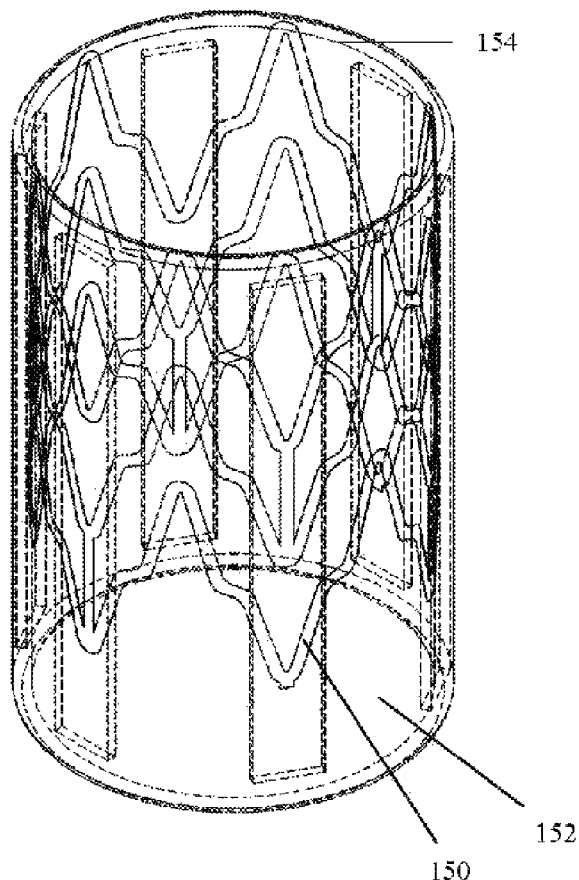
FIGS. 16A-C depict resilient mesh that can be embedded in the structure of intragastric devices.
Figure 16B:
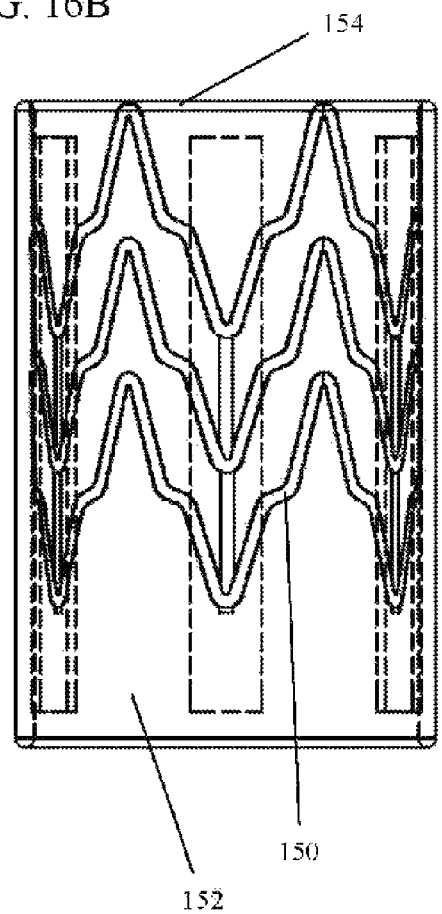
Figure 16C:
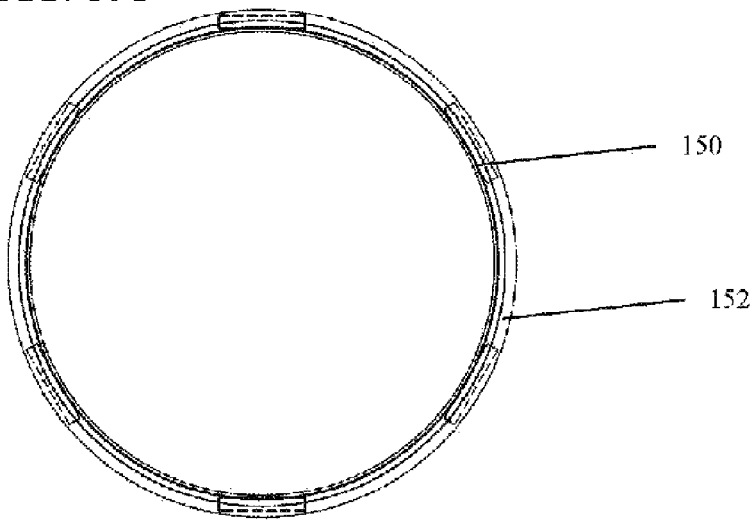

FIG. 15A is a perspective view of the collapsible intragastric device of FIGS. 14A-C with its unrestrained magnetic powder (140) in the upper portion of the 6 sealed compartments (142) due to the presence of an external magnetic device (148) positioned close enough to the intragastric device to create an attractive force between the magnetic powder and the external magnetic device sufficient to pull the intragastric device towards, and impart stimulating force upon, the inner wall of the patient's stomach to induce the feeling of satiety in the same manner depicted in, e.g., FIGS. 7A-B. FIG. 15B is a bottom plan view of the intragastric device depicted in FIG. 15A. FIG. 15C is a side elevation view of the intragastric device depicted in FIG. 15A.

Where increased rigidity or structural integrity is desired, e.g., during endoscopic insertion and retrieval, resilient mesh may be integrated in or attached to any intragastric device. Similarly, resilient mesh may also be attached to magnetic materials within the device to provide an extra degree of protection against separation of magnetic materials within the gastric lumen in the event that the structural integrity of a device becomes compromised. Finally, a suture loop may be threaded through resilient mesh to facilitate endoscopic collapse and removal of the device. FIG. 16A is a perspective view of resilient mesh (150) capable of being embedded in the structure of any intragastric device, and shown embedded in the collapsible tubular structure (152) of the intragastric device depicted in FIGS. 1A-B. A single suture loop (154) is also depicted, threaded through the upper portion of the mesh, which can be pulled away from the device to streamline transesophageal removal by reducing the circumference of the upper portion of the device and causing it to collapse inwards and push any stomach contents that may be residing in the device's hollow core out through the bottom of the device. While many additional methods of inserting and removing this intragastric device will be apparent to persons of ordinary skill in the art, tools appropriate for orienting the device within the gastric lumen and pulling the depicted suture loop may include without limitation biopsy forceps, suction cylinders, and endoscopic magnets. Other equipment and methods of streamlining suture recovery may be used as well, such as incorporating snare loops into the suture loop, and using a suture whose color is distinguished from the remainder of the device, FIG. 16B is a side elevation view of the resilient mesh (150) and intragastric device of FIG. 16A. FIG. 16C is a bottom plan view of the resilient mesh (150) and intragastric device of FIG. 16A.

Figure 17A:
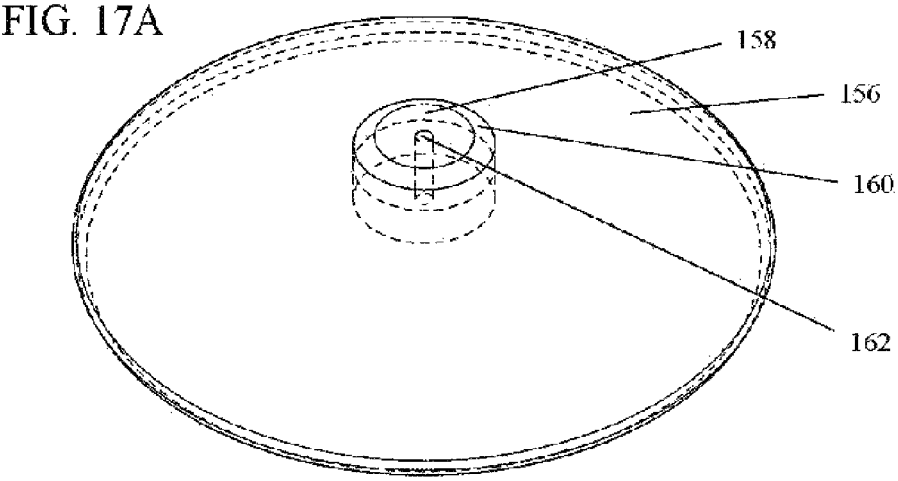
FIGS. 17A-C depict a frustacone-shaped collapsible intragastric device with a narrow central channel.
Figure 17B:
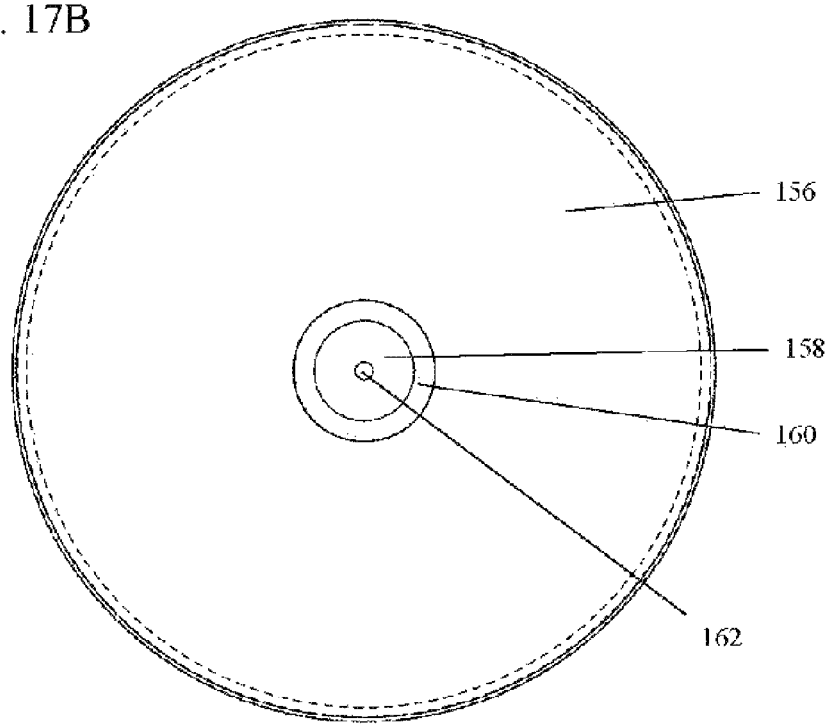
Figure 17C:
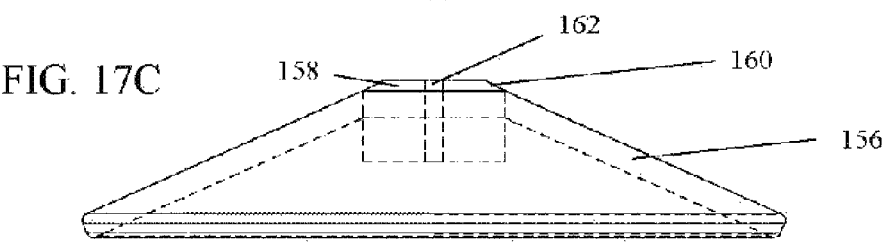

FIG. 17A is a perspective view of a collapsible cone-shaped intragastric device comprising a flexible and resilient frustacone-shaped structure (156) which encircles a cylindrical piece of magnetic material (158) with a chamfered edge (160) and narrow central channel (162), into which instruments may be inserted to securely grasp the device and dictate its orientation. In contrast to FIGS. 2A-C, this device's narrow central channel (162) is formed with additional magnetic material which envelops the hollow central channel, which also increases the amount of magnetic material in the device, and derivatively, the amount of pulling force that can be created in communication with an external magnetic device. When a reduction in the intragastric device's pulling force, weight, or collapsed size is desired, the outer diameter of the cylindrical magnetic material and inner diameter of the frustacone-shaped structure may be reduced by the same amount. Like many other embodiments, an external magnetic device may be used to attract the device of FIGS. 17A-C towards, and impart stimulating force upon, the inner wall of a patient's stomach to induce the feeling of satiety. FIG. 17B is a top plan view of the intragastric device of FIG. 17A. FIG. 17C is a side elevation view of the intragastric device of FIG. 17A.

Figure 18A:
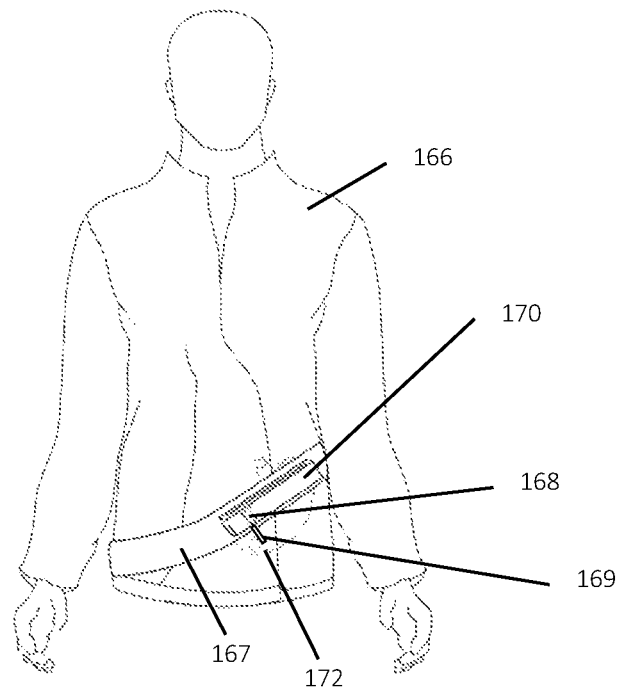
FIG. 18A is a perspective view of a belt containing an external magnetic device in the lower position.
Figure 18A:

Yet another embodiment of the satiety-inducing system addresses the need for predictable positioning of the external magnet, as well as practical means for carrying it around throughout the day. FIG. 18A is a perspective view of a belt containing an external magnetic device in the lower position. FIG. 18A shows a piece of apparel (166) such as a shirt being worn by a patient. A belt (167) is strapped across the waste of the patient. Attached to belt (167) is a magnet container device (170) which contains an external magnet (168) attached to a handle (169). The patient uses the handle to move the external magnet (168) from a lower position to a higher position and vice versa. In alternative embodiments, the external magnet surface is covered with a coating (such as plastic or teflon), and the handle and the plastic casing could be one unit. That is, FIG. 18A shows the external magnet (168) in the lower position, with intragastric device (172) in the bottom portion of the patient's stomach. A patient has the ability to move the intragastric device (172) towards the stomach wall by putting on the belt with the external magnetic device in the lower position, capturing the floating intragastric device in a lower position and then moving the external magnet (168) to an upper position, such as in FIG. 18B, such that the intragastric device is pressed against the stomach wall to induce a feeling of satiety.

Figure 18B:
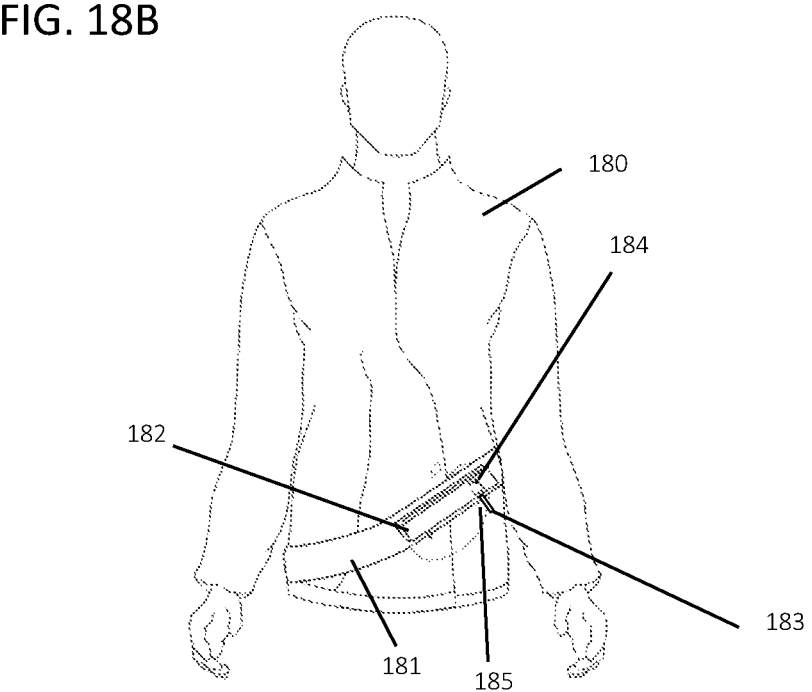
FIG. 18B is a perspective view of an belt containing an external magnetic device in the upper position.

FIG. 18B is a perspective view of a belt containing an external magnetic device in the upper position. FIG. 18B shows a piece of apparel (180) such as a shirt being worn by a patient. A belt (181) is strapped across the waist of the patient. Attached to the belt (181) is a magnet container device (182) which contains an external magnet (184) attached to a handle (183) in an upper position, which is close enough to the intragastric device (185) to create a strong pulling force between the external magnet (184) and intragastric device (185) such that the intagastric device is pressed against the stomach wall of the patient. The patient can use handle to move the external magnet (168) back from the higher position to a lower position.

Ghrelin or the "hunger hormone", also known as lenomorelin (INN), is a peptide hormone produced by ghrelinergic cells in the gastrointestinal tract. When the stomach is empty, ghrelin is secreted. When the stomach is stretched, secretion stops. It can be appreciated that moving an external magnet from a lower position such as that shown in FIG. 18A to an upper position such as that shown in FIG. 18B would stimulate and expand the inner stomach wall and thus stop secretion of the hormone ghrelin, thus adding to the feeling of satiety of the patient.

Figure 19A:
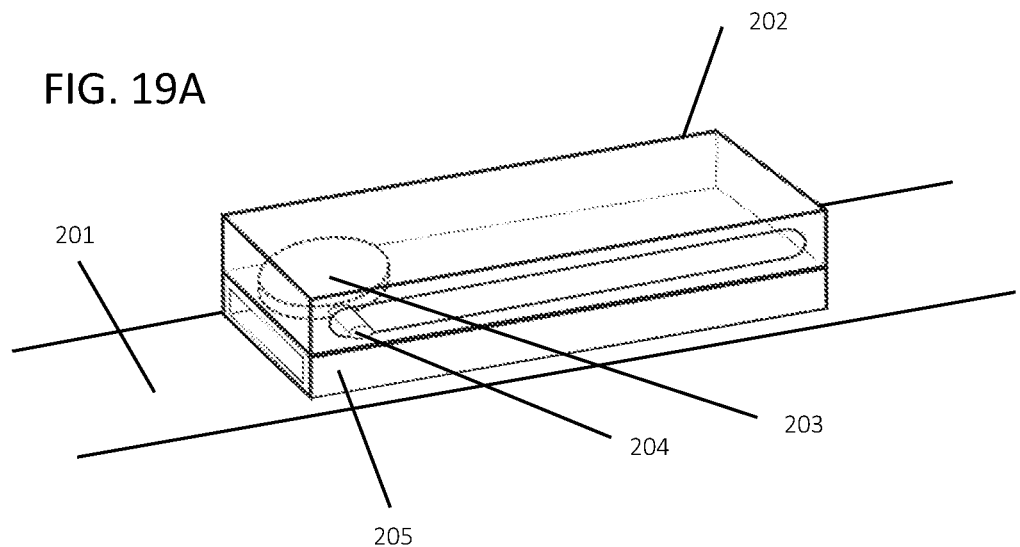
FIG. 19A illustrates an embodiment of a magnet container device.

FIG. 19A illustrates an embodiment of a magnet container device (202). In the depicted figure, a magnet container device (202) is attached to a belt (201) which is intended to be strapped across the waste of a patient. External magnet (203) comprises a permanent magnet source which is intended to attract an intragastric device. Attached to external magnet (203) is a handle (204) which is used by a patient to move the external magnet from a lower position to an upper position, thus moving an intragastric device comprised of magnetic material to an upper position within the stomach.

The embodiment shown in FIG. 19A addresses the situation where it may be desirable to immediately cut off the magnetic force of the external magnet. To accomplish this, magnet container device (201) contains a shield chamber (205) where a patient can slide in a shield which interferes with the magnetic field. In alternative embodiments, a shield can be deployed after external magnet is in an upper position for a predetermined amount of time. For example, a timer could be triggered when the external magnet is moved into an upper position and reset when the external magnet is moved back into a lower position. The shield could be automatically deployed via a simple sliding mechanism when the timer reaches 30 minutes. This timer could be utilized as a safety measure in case the patient forgets to move the magnet back into a lower position, so that the intagastric device does not remain pushed against the stomach wall of the patient.

Figure 19B:
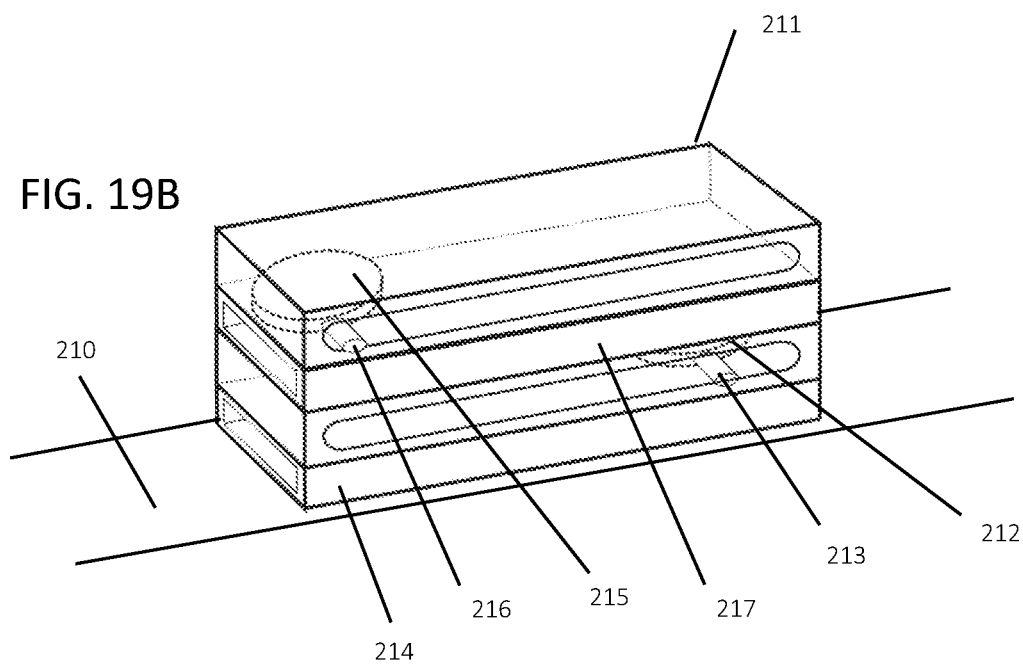
FIG. 19B is an embodiment of a magnet containing device where a second external magnet is utilized to create additional force.

In some embodiments, the magnet container device has additional features where the simplicity of the design of magnet container device 201 is not desired. The magnet container device (211) depicted in FIG. 19B displays an example of such an embodiment. FIG. 19B is an embodiment of a magnet containing device where a second external magnet (215) is utilized to create additional force. It can be appreciated that two identical magnets stacked directly on top of each other behave similar to a solid magnet of the same dimensions as the two stacked magnets. Thus, magnet container device (211) advantageously provides added flexibility in adding and removing additional magnetic force by utilizing a second magnet to create additional force. For example, a patient may require more force to grab the intragastric device at a lower position, so both magnets could be utilized at the lower position and moved to a top position. When the patient wants to create additional force, the patient can move the second external magnet (215) towards the upper position via a second handle (216). That is, when an addition of the pulling force in the upper position is desired, the embodiment illustrated as magnet container device 301 advantageously provides a second external magnet.

Alternatively, when the patient wants to create additional force at a lower position to grab the intragastric device, the patient can have both external magnets (215) in the lower position and move them both to the upper position. Once the intagastric device has been captured and moved to the upper position, the second external magnet can be moved back to reduce the force at the upper position.

Magnet container device (201) also contains an upper shield chamber (217) for interfering between the two external magnets, as well as a lower shield chamber (214) where a patient can cut off the magnetic attraction with the intragastic device.

Figure 20A:
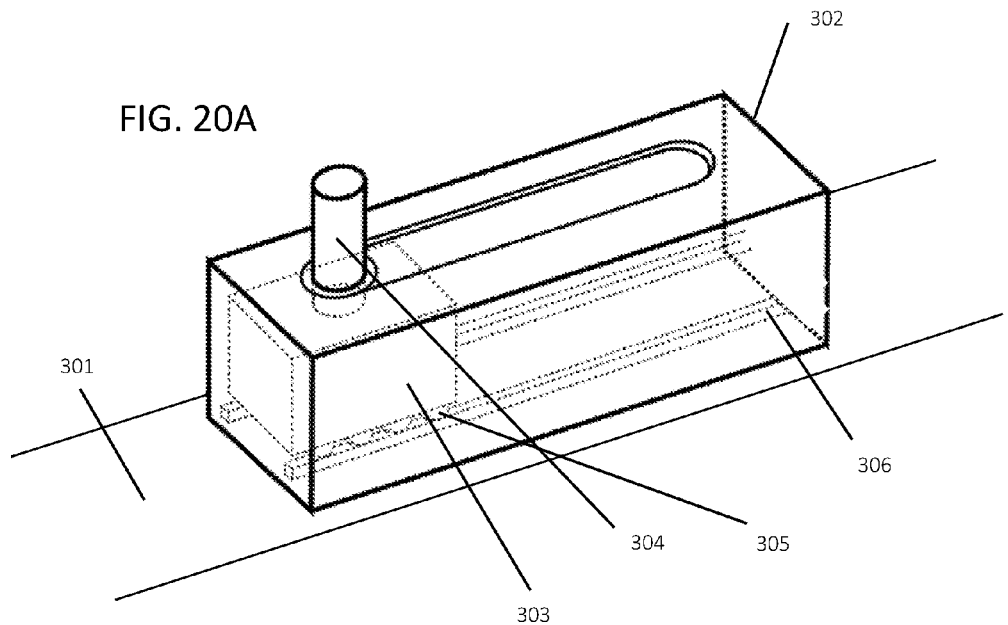
FIG. 20A illustrates an embodiment of a magnet container device which provides for moving an external magnetic device.

The present disclosure provides for multiple embodiments for a patient positioning an external magnetic device by moving the external magnetic device from a lower position to a upper position. FIG. 20A illustrates an embodiment of a magnet container device (302) which provides for moving an external magnetic device. Magnet container device (302) contains an external magnet (303) attached to a handle (304). The external magnet has wheels (305) which run on tracks (306) which are mounted on the bottom of magnet container device (302). A patient moves the external magnet via handle (304) from a lower position to an upper position, and vice versa.

Figure 20B:
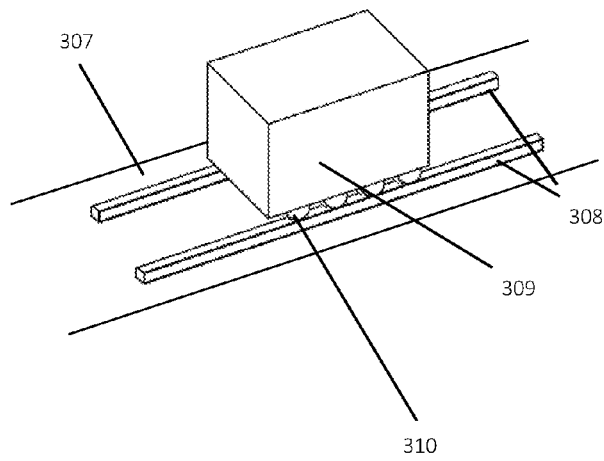
FIG. 20B illustrates a track mechanism for moving an external magnet.

FIG. 20B illustrates a track mechanism for moving an external magnet (309) where the magnet (309) has wheels (310) that runs on a track (308) which is directly attached to belt (307). It can be appreciated that this embodiment does not utilize a magnet container device, and a patient simply grabs the external magnet directly to moves it along the track from a lower position to an upper position, and vice versa.

Figure 20C:
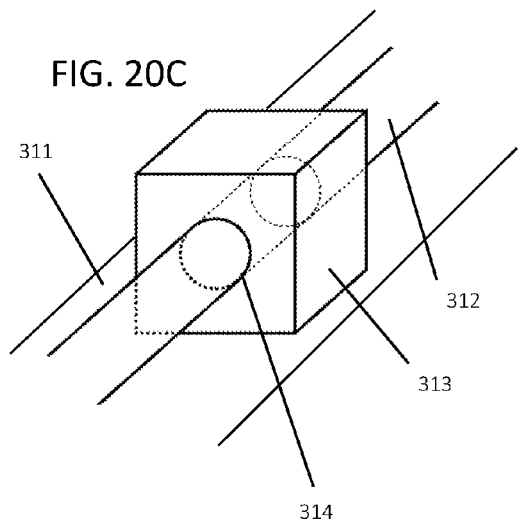
FIG. 20C illustrates a rail mechanism for moving an external magnet.

FIG. 20C illustrates a rail mechanism for moving an external magnet whereby the external magnet (313) contains a hole(314), and a rail (313) attached to a patient's belt (311) is run through a hole (314). It can be appreciated that this embodiment does not utilize a magnet container device or a track, and a patient simply grabs the external magnet directly to moves it along the rail (313) from a lower position to an upper position, and vice versa.

In some embodiments, the mechanism for moving the external magnet does not include wheels, rails, or tracks. For example, in one embodiment the inner walls of the magnetic container device are covered with a smooth material such as felt to reduce friction with the magnet, such that the external magnet can be moved smoothly by a patient using handle without the use of wheels or a track. In such embodiments, the magnet is sized to snugly fit the magnetic container device such that it can smoothly be run along the magnetic container device without utilizing any rails or tracks.

Figure 21A:
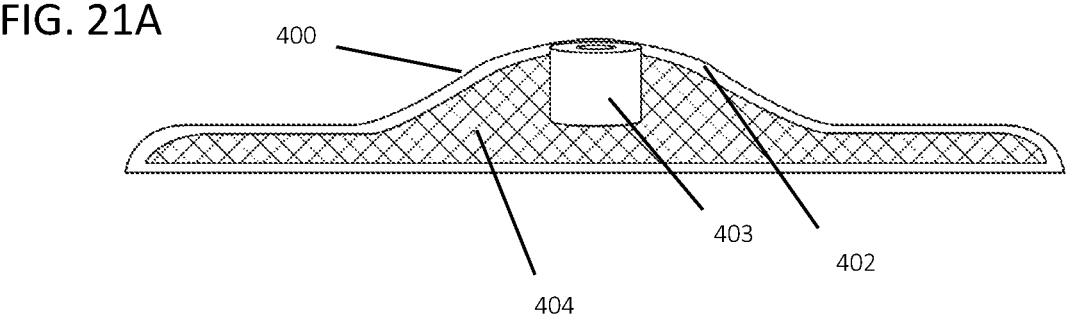
FIG. 21A illustrates a cross sectional view of an embodiment of a saucer shaped intragastric device.
Figure 21B:
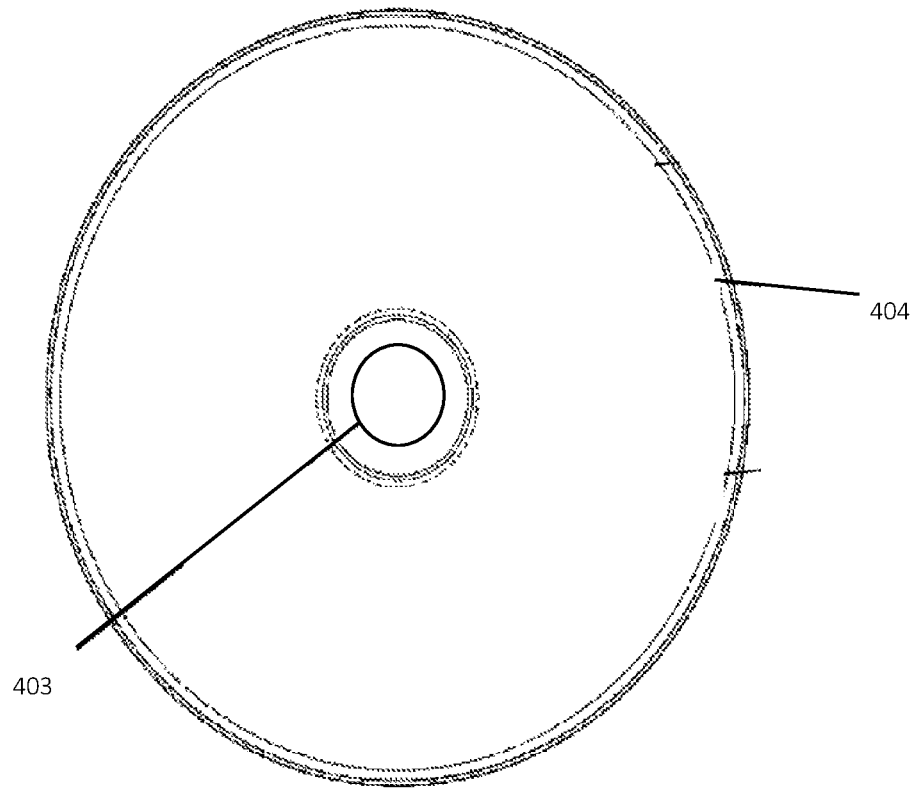
FIG. 21B is a top plan view of the intragastric device depicted in FIG. 21A.

FIG. 21A illustrates a cross sectional view of an embodiment of a saucer shaped intragastric device (400). The intragastric device has a plastic exterior cover (401) and an outer wall (402) comprised of a soft material such as silicone which is designed not to scratch injure the stomach wall of the patent. An internal magnet (403) is positioned at the apex of the intragastric device (400). The intagastric device is covered by a resilient mesh (404). FIG. 21B is a top plan view of the intragastric device depicted in FIG. 21A.

Figure 22A:
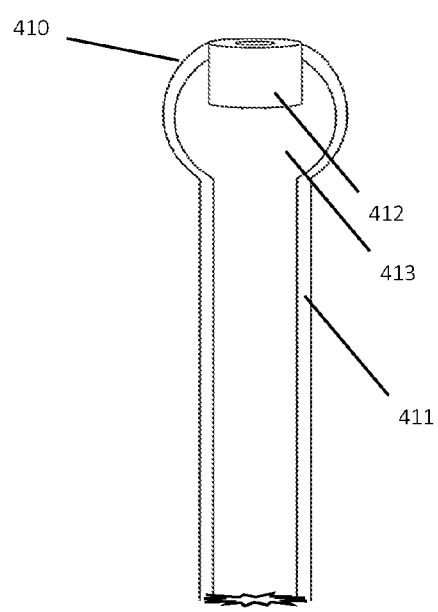
FIG. 22A illustrates a cross-sectional view of an intragastric device (410) in a collapsed state.

FIG. 22A illustrates a cross-sectional view of a zig-zag intragastric device (410) in a collapsed state for insertion into a patient's stomach via their esophagus. The intagastric device has a plastic exterior cover and an outer wall (411) comprised of a soft material such as silicone which is designed not to scratch injure the stomach wall of the patent. An internal magnet (412) is positioned at the apex of the intragastric device (400), wherein the internal magnet has a hole passing through it so that the intragastric device can be guided into the patients stomach. Once such a resilient collapsible device exits the esophagus and enters the stomach, the device's resilient and flexible structure reverts to its natural deployed state, as shown in FIG. 22B.

Figure 22B:
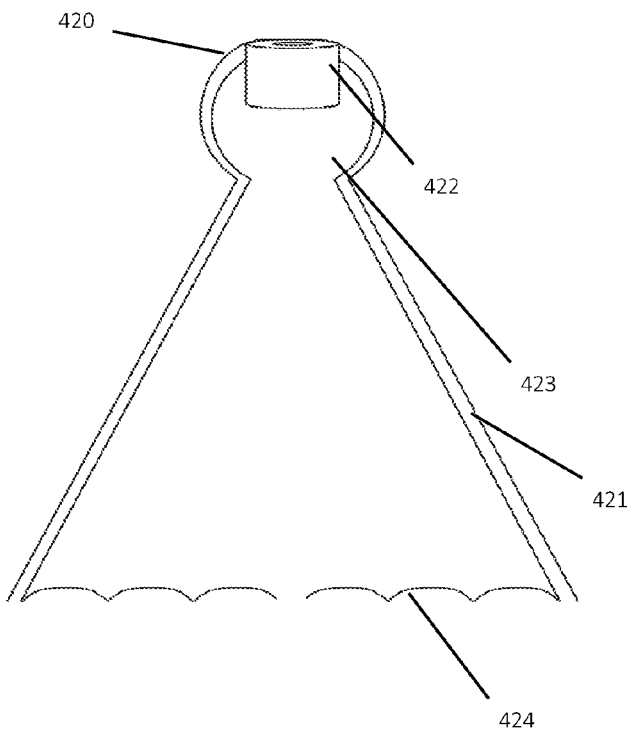
FIG. 22B illustrates a cross-sectional view of a zig-zag intragastric device (420) in an expanded state.

FIG. 22B illustrates a cross-sectional view of a zig-zag intragastric device (420) in an expanded state. An internal magnet (403) is positioned at the apex of the intragastric device (400). The bottom zig-zag edge (424) contains ridges designed with a zig-zag shape such that even if the bottom of the intragastic device is pressed against the stomach wall, digestive material such a food can still pass the ridges of the zig-zag surface. That is, the grooved surface is such that there will always be a gap between the intagastic device and the stomach wall, such that food and other materials can still pass through and around the intragastric device.

Figure 22C:
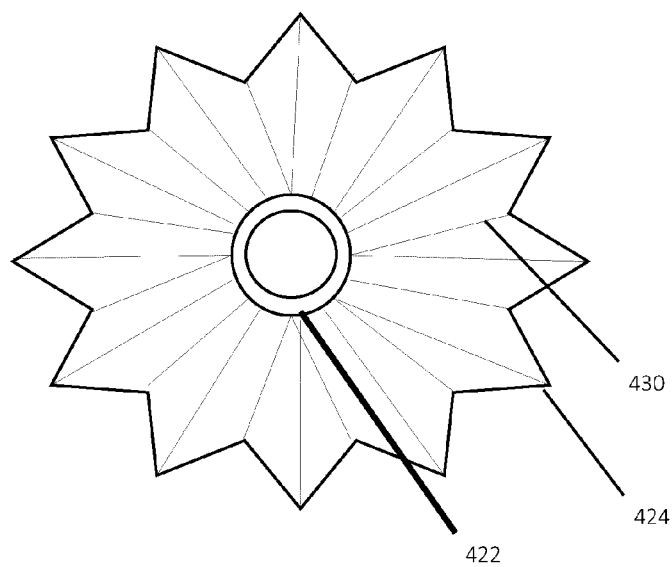
FIG. 22C is a top plan view of the zig-zag intragastric device depicted in FIG. 22B.

FIG. 22C is a top plan view of the zig-zag intragastric device in an expanded state depicted in FIG. 22B. It can be appreciated that ridges (430) extend from the end of the device all the way to the magnet at the apex.

It is to be understood that the above-referenced arrangements are illustrative of the application for the principles of the present invention. Numerous modifications and alternative arrangements can be devised without departmg from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

The invention claimed is:

1. A method of inducing a feeling of satiety comprising the steps of:
   a) transesophageal insertion of a deployable intragastric device containing magnetic material into a stomach of a patient;
   b) deploying the intragastric device within the stomach, wherein the intragastric device is not attached to the body; and
   c) positioning an external magnet in close enough proximity to the intragastric device to create a sufficient magnetic pulling force between the external magnet and the intragastric device to move the intragastric device towards, and impart stimulating force upon a stomach wall of the patient, wherein the patient positions the external magnet and the stimulating force is applied for a therapeutically sufficient period of time to induce a feeling of satiety in the patient, and wherein the patient positions the external magnet by moving the external magnet from a lower position to an upper position to induce the feeling of satiety.

2. The method of claim 1, wherein the external magnet is located within a magnetic container device.

3. The method of claim 2, wherein the magnetic container device contains a second magnet which the patient positions on top of the external magnet to create additional force, and wherein the magnetic container device is located on a belt worn by the patient.

4. The method of claim 3, wherein the second magnet is moved back into a lower position after the patient has moved both the first magnet and the second magnet into an upper position.

5. The method of claim 1 further including exposing the external device to at least one compound of high magnetic permeability to:
   a) prevent interference with, or attraction to, other magnetically sensitive objects, or b) adjust the magnetic pulling force applied to the intragastric device by diverting a magnetic field of the external device away from the intragastric device.

6. The method of claim 1, wherein the intragastric device comprises a frustacone-shaped structure with a ring magnet affixed to an apex of the intagrastric device.

7. The method of claim 6, wherein the intragastric device contains a hollow central core.

8. A satiety inducing system comprising:
a) a transorally administered intragastric device comprising at least one type of magnetic material, at least one surface capable of deployment inside of a stomach, wherein the intragastric device is equipped to impart tactile stimulation upon a stomach wall of the stomach, and wherein the intragastric device is not attached to the body; and
b) an external magnet positioned outside of a patient's body comprising a sufficient amount of magnetic material to attract the transorally administered intragastric device from outside the patient's body, wherein the patient positions the external magnet by moving the external magnet from a lower position to an upper position to induce a feeling of satiety in the patient.

9. The system of claim 8, further comprising a magnetic container device wherein the external magnet is located within the magnetic container device.

10. The intragastric device of claim 8 wherein an orientation of external magnet's magnetic material is unfixed and allowed to pivot or rotate relative to the position of the intragastric device.

11. The system of claim 8 wherein the external magnet is located on a belt worn by the patient.

12. The system of claim 9 wherein the magnetic container device further comprises a second external magnet located within the magnetic container device.

13. The intragastric device of claim 8 further including a fluid bladder that can be inflated to deploy the intragastric device.

14. The intragastric device of claim 8 wherein the at least one type of magnetic material is unrestrained and confined within a fluid bladder or seated compartment.

15. The intragastric device of claim 8 further including a biocompatible dye confined within a fluid bladder or sealed compartment.

16. The intragastric device of claim 8 wherein comprises iron, steel, or neodymium.

17. The system of claim 8 wherein the at least one surface of the intragastric device is textured.

18. The intragastric device of claim 8 further including a resilient mesh embedded in or attached to the intragastric device.

19. The intragastric device of claim 8 further including at least one suture loop embedded in the intragastric device.

20. The intragastric device of claim 8, wherein the external magnet further comprises an electromagnet connected to a battery and a control switch.

* * * * *